United States Patent [19]
Cho

[11] Patent Number: 5,858,398
[45] Date of Patent: Jan. 12, 1999

[54] MICROPARTICULAR PHARMACEUTICAL COMPOSITIONS

[75] Inventor: Young W. Cho, Cincinnati, Ohio

[73] Assignee: Isomed Inc., Apopka, Fla.

[21] Appl. No.: 635,945

[22] PCT Filed: Nov. 3, 1994

[86] PCT No.: PCT/US94/12351

§ 371 Date: May 2, 1996

§ 102(e) Date: May 2, 1996

[87] PCT Pub. No.: WO95/12385

PCT Pub. Date: May 11, 1995

[51] Int. Cl.⁶ .............................. A61K 9/14; A61K 9/48; A61K 9/127

[52] U.S. Cl. .......................... 424/450; 424/456; 424/489; 514/937; 514/941

[58] Field of Search ........................... 424/450, 489, 424/456, 490–502; 514/937–943

[56] References Cited

U.S. PATENT DOCUMENTS

| | | | |
|---|---|---|---|
| 4,146,499 | 3/1979 | Rosano | 252/186 |
| 4,348,384 | 9/1982 | Horikoshi et al. | 424/101 |
| 4,356,167 | 10/1982 | Kelly | 424/38 |
| 4,536,324 | 8/1985 | Fujiwara et al. | 252/311 |
| 4,579,730 | 4/1986 | Kidron et al. | 424/19 |
| 4,649,075 | 3/1987 | Jost | 428/305.5 |
| 4,719,239 | 1/1988 | Muller et al. | 514/785 |
| 4,801,734 | 1/1989 | Kock et al. | 560/73 |
| 4,837,028 | 6/1989 | Allen | 424/450 |
| 4,849,227 | 7/1989 | Cho | 424/498 |
| 4,855,090 | 8/1989 | Wallach | 264/4.1 |
| 5,023,252 | 6/1991 | Hsieh | 514/183 |
| 5,250,236 | 10/1993 | Gasco | 264/4.4 |
| 5,550,225 | 8/1996 | Philippe | 536/115 |

FOREIGN PATENT DOCUMENTS

| | | |
|---|---|---|
| 841369 | 11/1985 | Brazil . |
| 130779 | 1/1985 | European Pat. Off. . |
| 0140085 | 5/1985 | European Pat. Off. . |
| 143949 | 6/1985 | European Pat. Off. . |
| 0277776 | 8/1988 | European Pat. Off. . |
| 0339994 | 11/1989 | European Pat. Off. . |
| 2581543 | 11/1986 | France . |
| 3406497 | 2/1984 | Germany . |
| 84-182724 | 3/1986 | Japan . |
| WO8605694 | 10/1985 | WIPO . |
| WO8505036 | 11/1985 | WIPO . |
| WO8703473 | 6/1987 | WIPO . |
| WO8801213 | 2/1988 | WIPO . |
| WO8900812 | 2/1989 | WIPO . |
| WO9003164 | 4/1990 | WIPO . |
| WO9114454 | 10/1991 | WIPO . |

OTHER PUBLICATIONS

Hackh's Chemical Dictionary (3d ed. 1950), pp. 787 and 541.
The Van Nostrand Chemist's Dictionary (1953), p. 281.
Morrison & Boyd, Organic Chemistry, (3d ed. 1976), p. 1057.
McCutcheon's Emulsifiers & Detergents, 1987 North American Edition, HLB Index of Materials (Hydrophylic Lipophylic Balance), pp. 287–312.
Vol. 4, Encyclopedia of Chemical Technology (R. Kirk and D. Othmer, eds. (1954)), pp. 939–940.
Van Nostrand's Chemical Dictionary, p. 281 (1953).
Inouye, W.Y. et al., Surg. Forum 13:316 (1962).
Danforth, E. et al., Endocrinology 65:118 (1959).
Crane, C.W. et al., Diabetes 17:625 (1968).
Muranishi, S. et al., J. Pharm. Dyn. 1:28 (1978).
Muranishi, S. et al., J. Pharm. Dyn. 2:286 (1979).
Muranishi, S. et al., Int. J. Pharm. 4:219 (1980).
Galloway, J.A. et al., Diabetes 21:637 (1972).
Meshia, M.S. et al., J. Pharm. Pharmacol. 33:733 (1981).
Kawamori, R. and Shichiri, M., Diabetes (1982) in Int. Cong. Ser. 600:315 (1983).
Oppenheim, R.C. et al., Drug Dev. Ind. Pharm. 8:531 (1982).
Kawamon et al., Int. Cong. Ser. 600:315 (1983).
Roger, H.J. et al., Diabetologia 23:37 (1982).
Yokoyama, M. et al., Makromol. Chem. 8:431 (1987).
Kopecek, J., Advanced Drug Deliv. System 4 (ed. by Anderson, J.M. et al.).
Patel, H.M. et al., FEBS Letters 62:60 (1976).
Dapergolas, G. et al., Lancet 2:824 (1976).
Tagesson, C. et al., Gut. 26:369 (1985).

Fabre, H. et al., J. Phys. Chem. 85: 3493, (1981).
Liu, J.C., Internat. J. Pharm. 44: 197 (1988).
Nagai, T.J., Controlled Release 2:121 (1985).
Kazim, M. et al., Surg. Forum 35: 64 (1984).
Bowman, W.C. & Rand, M.J., *Textbook of Pharmacology*, 2nd ed., p. 16.3 (1980).
Larsen, K. et al., Chem. Phys. Lipid, 12:321 (1980).
Longley, W. et al., Nature 303:612 (1983).
Larsson, K. et al., J. Colloid, Interface Sci. 72: 152, (1979).
El–Nokaly, M. et al., J. Colloid Interface Sci. 84:228 (1981).
Ekwall, P., Advances, Liquid Crystals, vol. 1, Chapter 1, Academic Press, N.Y. (1975).
Proksch et al., Clin. Chem. 24/11:1924–26 (1978).
M. Kates, Techniques in Lipidology, (Elsevier, Amsterdam (1972)).
Chung, K.H., Chung, J.S. & Cho, Y.W.: Presented at 13th Congress International Soc. Thrombosis & Homeostasis, Jul. 3, 1991, Utrecht.
H. Brockerhoff and M. Yurkowski, Canadian J. Biochem. 43:1777 (1965).
Rydhag. L. et al., J. Am. Oil Chem. Soc. 58:830 (1981).
Morrison & Boyd, Organic Chemistry, (3d ed. 1976), p. 1057.

*Primary Examiner*—Gollamudi S. Kishore
*Attorney, Agent, or Firm*—Baker & Botts, L.L.P.

[57]     ABSTRACT

A pharmaceutical composition comprises microparticles in micelle. The microparticles contain at least one pharmaceutically-active agent, at least one water soluble or miscible phospholipid, at least one lipid soluble or miscible phospholipid, at least one non-ionic surfactant having an HLB value of about 15 or greater, at least one non-ionic surfactant having an HLB value of about or less, and at least one water soluble or miscible sterol compound. The microparticles are suspended in at least one fatty acid having a chain length of $C_{14}$ or less. The composition may optionally contain at least one fatty acid having a chain length of $C_{16}$ or greater in a concentration of about 5 w/v % or less. The composition is prepared by admixing the pharmaceutically-active agent, phospholipids, surfactants, and sterol, micronizing the admixture to form microparticles, and suspending the microparticles in at least one fatty acid of chain length of $C_{14}$ or less to form microparticles in micelle. The invention may be useful in the oral administration of drugs and other therapeutic agents, as well as for the trans-umbilico-dermal administration of such drugs and therapeutic agents.

15 Claims, 2 Drawing Sheets

MICROPARTICULAR PHARMACEUTICAL COMPOSITIONS

This application is a 371 of PCT/US94/12351 filed Nov. 3, 1994.

BACKGROUND OF THE INVENTION

The present invention relates generally to pharmaceutical compositions comprising microparticles suspended in micelle. More particularly, the microparticles comprise at least one pharmaceutically-active agent, at least one water soluble or miscible phospholipid, at least one lipid soluble or miscible phospholipid, at least one water soluble or miscible sterol, at least one non-ionic surfactant having an HLB value of about 15 or greater, and at least one non-ionic surfactant having an HLB value of about 6 or less, and the microparticles are suspended in micelle in at least one water soluble or miscible fatty acid having a chain length of $C_{14}$ or less. This invention also relates to a method of preparing such compositions, methods of therapeutically treating various illnesses and conditions with such compositions, and methods of delivery of such compositions to human beings.

By binding a pharmaceutically-active agent (e.g. insulin) in accordance with this invention, enhanced bioavailability and bioactivity results from the bound pharmaceutically-active agent. For example, after oral or transdermal administration of the embodiment of this invention where insulin is the pharmaceutically-active agent, the composition is channeled into the liver, where the initially protected insulin is gradually released, mimicking an endogenously secreted insulin as found in human beings. An exogenous insulin, for example, has been successfully delivered by routes other than parenteral injection. The compositions of this invention may be applied by rectal, buccal, sublingual, intranasal, intrapulmonic, ocular or by other means of administration for management of disorders, for example diabetes mellitus. The compositions may be delivered selectively, after parenteral infusion, oral, transdermal, or other means of administration to achieve precise targeting of the pharmaceutically active agent to a given organ or tissues as a slow, controlled release-dosage formulation. The invention may be useful for, but not limited to, delivering pharmaceutically-active agents which include peptides (e.g. insulin), glycoproteins (e.g. erythropoietin), organic and inorganic chemicals (e.g. glyburide or steroids), herbals (e.g. vinca alkaloids), and other materials useful as pharmaceutically active agents.

For example, diabetes mellitus is a chronic disorder affecting carbohydrate, fat and protein metabolism. It is generally characterized by high blood sugar level (hyperglycemia) and sugar in urine (glycosurea) from a defective or deficient insulin secretory response. In the United States, over 10 million people are diagnosed as diabetics and this figure is increasing annually at a rate of about 6%. Two major variants of the disease exist. For about 10% of diabetics, the disease onsets as a juvenile insulinopenic diabetes requiring daily injection of insulin (referred to herein as insulin dependent diabetics or IDDM). The majority of diabetics are adult-onsetting diabetics (referred to herein as non-insulin dependent or NIDDM) for whom oral antihyperglycemics may be introduced to control hyperglycemia and glycosurea. Such compounds include chlorpropamide, tolbutamide (the first generation group of sulfonylureas), glyburide and glipizide (the second generation group). The sulfonylureas are believed to stimulate the beta cells of the pancreas, causing secretion of an endogenous insulin, and are also known to reduce hepatic production and to increase peripheral muscular utilization of glucose.

Ultimately, however, sulfonylureas will become less effective and eventually totally ineffective in lowering blood sugar in many long-term NIDDM patients, thus requiring injections of insulin as well, which causes restoration of the bioactivity of the sulfonyl urea (e.g. glyburide). According to one embodiment of the present invention, insulin-containing compositions of this invention, glyburide-containing compositions of this invention, and their combination markedly improved the bioavailability and activity of glyburide and oral insulin in NIDDM patents, who typically resist commercial glyburide and thus require daily injections of insulin.

Another embodiment of the present invention is directed to trans-umbilico dermal (referred to herein as TuD) delivery systems of the above-described compositions in human beings. More specifically, the TuD drug delivery system is concerned with well protected pharmaceutically-active agent or agents prepared in accordance with the compositions of this invention which are channeled into the liver, where the protected agent is released at a slow controlled rate, inducing the bioactivity of such compounds. In accordance with the present invention, the composition or compositions are applied on the dermal area of the human navel, that is the falciform ligament (paraumbilical veins) and its related system. The falciform ligament and Lig. teres in the liver, which are connected to tributaries of the epigastric veins and around the umbilicus, form anastomoses between the portal and the systemic venous systems. The umbilical foci is different from ordinary dermal layers. It is an artificially made scar tissue, having a thin epidermal layer with a direct connection to the falciform ligament (paraumbilical veins) and the epigastric vein. After applying the compositions of the present invention via the trans-umbilico-dermal delivery system to the navel foci, the compositions are rapidly and readily absorbed via the falciform ligament, and distributed within the liver and the systemic venous system. The trans-umbilico-dermal delivery of compositions of the present invention may also be employed as a means of targeting cancer chemotherapeutics (e.g. doxorubicin) into the liver, uterus, ovaries, lungs, the gastrointestinal system including the stomach, rectum, colon, etc. as well as other organs and systems.

By replacing inhibitors (e.g. nonulosaminic acid) with potentiators (e.g. a triantennary galactose terminated cholesterol), an affinity to the macrophageal system may be modified and it is possible to make compositions of this invention which can be predominantly channeled into the liver and other reticuloenthothelial systems (RES), thereby modifying the bioactivity of the pharmaceutically active agents employed while the systemic blood concentrations of such agents are kept at relatively low, non-toxic, non-side effect-inducing levels. Such hepato-specific delivery system-bound compositions may be given orally, rectally, trans-umbilico-dermally, parenterally or by other means. The therapeutic efficacy (i.e. the ratio between the side effect or toxic dose over the effective dose) of the agent may be increased by its binding in accordance with this invention. This may be exemplified as follows: disulfiram is biotransformed in the liver, forming an active diethyl dithiocarbamic acid; benzamidosalicylate forms amino-salicylic acid; biguanide forms cycloguanil; diazepam forms oxazepam; imipramine forms desipramine; phenacetin is activated in forming paracetamol; phenytoin forms di-phenyluredoacetic acid, and so forth. Also, the therapeutic effectiveness of pharmaceutically active agents may be induced by their transportation into the liver, where the agent or agents are actively biotransformed into therapeutically effective agents. For example, the antimalarial activity of primaguine as a pharmaceutically active agent is increased by its intrahepatic biotransformation into quinone derivatives while the side effects are reduced.

The present invention is dissimilar from other types of drug or pharmaceutical agent delivery systems. For example, compared to other routes, oral administration of compositions of the present invention containing insulin are more acceptable and convenient for diabetics. More particularly, absorption of insulin from the intestines to cause lowering of blood glucose levels has been reported when pancreatic enzymes are inactivated (Inouye, W. Y. et al. in Surg. Forum 13:316 (1962); Danforth, E. et al. in Endocrinology 65:118 (1959); and Crane, C. W. et al. in Diabetes 17:625 (1968)). However, the absorption of non-degradated insulin was found to be poor. To promote absorption of the macromolecules (e.g. insulin) from the intestinal membrane, surfactants, triglycerides, and lipid-surfactant mixed micelles have been reported with poor or unsatisfactory results (Muranishi, S. et al. in J. Pharm. Dyn. 1:28 (1978); J. Pharm. Dyn. 2:286 (1979); Int. J. Pharm. 4:219 (1980); Inouye et al., Danforth et al., and Crane et al.).

Insulin and a few adjuvants (anticholinergics) have been combined with a non-ionic surfactant (i.e. BRIJI 98), causing absorption of insulin; however, the minimum effective dose of insulin in human beings was too large (Galloway, J. A. et al. in Diabetes 21:637 (1972)). The non-ionic surfactant BRIJI 58 combined with insulin was found to be effective in increasing intestinal absorption of insulin, but the effective dose of insulin required was too large (Meshia, M. S. et al. in J. Pharm. Pharmacol. 33: 733 (1981)). After a water-oil-water (w-o-w) emulsion form of insulin was administered into a ligated jejunal pouch in rabbits, less than 8% absorption of insulin was reported, which was increased to about 58% of absorption of insulin administered as w-o-w micelle into the ligated jejunal pouch (Kawamori, R. and Shichiri, M. in Diabetes (1982) in Int. Cong. Ser. 600:315 (1983)). An oral insulin in nanoparticles was reported in Oppenheim, R. C. et al., Drug Dev. Ind. Pharm 8:531 (1982), but a large dose of insulin was needed. (Galloway et al.; Meshia et al.; Kawamon et al., Int. Cong. Ser. 600:315 (1983); Oppenheim et al.).

U.S. Pat. No. 4,146,499 (Rosano) discloses several methods for preparing oil-in-water (o-in-w) forms of microemulsion systems by applying an amphiphatic surfactant into the oil phase, and a second surfactant having its HLB value above the primary surfactant into the aqueous phase of water or buffer solutions. The oil soluble substance is dissolved in the solvent (e.g light mineral oil) having low boiling hydrocarbons (e.g. hexane), halocarbons containing a hydroxy group (e.g. carbon tetrachloride), and water immiscible oxygenated hydrocarbons (e.g. diethyl ether). The dispersion of the oils into the aqueous solvent converts the lactescent in dispersion into a microemulsion. No data on its biologically applicable efficacy are given.

Although the oral insulin forms obtained from the above-cited references may be absorbed from the intestinal membrane with limited efficiency, they apparently are inactivated at the liver and cleared by various macrophageal systems, which may include the Peyer's patch, various circulating scavenger blood cells, lymphoid tissues, the reticuloendothelial systems, and others.

U.S. Pat. No. 4,579,730 (Kidron et al.) discloses a pharmaceutical composition for the oral administration of insulin which comprises insulin, bile salt or its derivatives and a protease-inhibitor. The composition can be enterocoated not only to protect the delivery system in the stomach but also to make the mixture slow release within the intestinal tract, and after its oral absorption from the intestinal membrane, enable delivery through the portal vein into the liver. The formulation disclosed in Kidron may not survive in the liver, as there are no means of protecting the system in the liver (other than the protease-inhibitor added), and Kidron's sustained-releasing form for insulin in the intestine would cause it to be too slowly absorbed. Biological test results of the oral insulin disclosed in Kidron were found to be poor and even less active than some other systems of applying surfactants, such as micelle, o-in-w emulsions and others (Muranishi, S. et al.; Galloway, J. A. et al.; Kawamori, R. et al.). In contrast, in the present invention only nonionic surfactants are employed in conjunction with the water soluble or miscible sterol and phospholipid bound microparticles suspended in micelle.

Significantly altered pharmacokinetics and efficacy of a polyglycol suspension of glyburide after oral or intravenous infusion was reported by Roger, H. J. et al. in Diabetologia 23:37 (1982). A micelle-forming polymeric adriamycin was made by using polyethyleneglycol and polyaspartic acid, which prolonged the survival time of cancerous mice while toxicity was reduced (the particle size was about 46 nm measured by laser scattering). Also, the system decreased antigenicity and prolonged its half-life in the circulating blood. It is also known that polyethyleneglycol is a nontoxic, nonimmunogenic water soluble and biodegrading polymer, as disclosed by Yokoyama, M. et al. in Makromol. Chem. 8:431 (1987). This system was intraperitoneally injected into the mice. Water soluble and targetable polymeric drug carriers based on N-(2-hydroxypropyl)methacryl-amide (HPMA) were bound with, for example, 5-aminosalicylic acid and galactosamine as the targeting moiety to cancer cells, as reported by Kopecek, J. in Advanced Drug Deliv. System 4 (ed. by Anderson, J. M. et al., at 279–290 (1990)). In contrast, the present invention is not used in conjunction with any polymeric or co-polymeric systems, and is effective for oral or TuD delivery of peptides.

Liposomes have been used as an oral delivery system for insulin. However, liposomes have shown a lack of dose-responsiveness, and inter- and intra-patients variations in the bioavailability and efficacy of insulin were noticed (Patel, H. M. et al. in FEBS Letters 62:60 (1976); Dapergolas, G. et al. in Lancet 2:824 (1976)). A modified liposome and a multiple emulsion has been disclosed in Eur. Pat. Appln. No. 0140085 (Yoshida). A drug containing lipid vesicle was prepared by stir-mixing an aqueous solution with phospholipids containing lipophilic surfactant. The lipid vesicles were dispersed in a dispersion medium and were freeze or spray dried (Patel et al.; Dapergolas et al.).

Europ. Pat. Appl. No. 0277776 (Huang) discloses a solid core liposome obtained by encapsulating a polymer mixture of emulsified warm (70° C.) aqueous agarose and gelatin used as a topical or local administration as a sustained release drug carrier for an enzyme or peptide. This is similar to the system disclosed in U.S. Pat. No. 5,250,236 (Gasco), discussed further herein.

U.S. Pat. No. 4,536,324 (Fujiwara et al.) discloses a lipovesicle form made by dispersing a nonionic surfactant into a hydrophilic or hydrophobic component in an isolated state from an aqueous dispersion medium. The vesicle is formed by polyoxyethylene castor oil ethers and polyoxyethylene hardened castor oil ethers in the presence of sorbitan polyesters of long chain (C14–C18) fatty acids. An oil component of cosmetics may be contained in the vesicle, which has as its membrane component a lipophilic surfactant.

U.S. Pat. No. 4,348,384 (Horikoshi et al.) discloses a pharmaceutical liposomal formulation containing coagulation Factor-VIII or IX and a protease inhibitor. The liposome forming materials were egg yolk lecithin, phosphatidic acid or phosphatidylserine (to improve the stability and forming ability of liposome), cholesterol (to strengthen the liposomal membrane), lyso-lecithin (to promote the fusion of the liposomal membrane with the membrane of absorptional cells), and phosphatidic acid (to enlarge the particle sizes of liposome).

However, Fujiwara et al.'s lipid vesicles and Horikoshi et al.'s liposome are entirely different from the phospholipid-bound pharmaceutically-active agents in the form of microparticles suspended in micelle of the present invention. Horikoshi et al. selected negatively charged phosphatidic acid (referred to herein as PA) or phosphatidylserine (referred to herein as PS), which was bound with a cholesterol moiety. These elements together may possibly mechanically stabilize and strengthen the liposomal membrane. However, in the present invention, the pharmaceutically active agent-containing microparticles are prepared by using a water soluble or miscible phospholipid (noncovalently bound with the agent) and then bound to a water soluble or miscible sterol, in conjunction with a lipid soluble or miscible phospholipid. For example, in the present invention a lysophospholipid (referred to herein as lyso-PL) such as lyso-phosphatidylcholine (referred to herein as lyso-PC) may be used to improve the adherence of the microparticle to the membrane of absorptive cells and to enable and induce an additive effect with the surfactants in a physiological manner without inducing any histopathological damage to intestinal membranes, which are known to be induced by lyso-PC at relatively higher concentrations, e.g. 0.01–1 mM (Tagesson, C. et al. in Gut. 26:369 (1985)).

French Pat. No. 85-06998 (Tressens) discloses a multi-vesicular liposome where the lipid phase consists of phosphatidylethanolamine (PE), cholesterol, PS, trioleine in chloroform and ether, while the aqueous phase contains an insulin—maltose solution. The multivesicular liposome was lyophilized and packed into intestinal capsules. In contrast, in the present invention the pharmaceutically active agent (e.g. insulin) is reversibly bound and made into a microparticle comprising a phospholipid such as a glycerophospholipid. The present invention is neither a liposome nor a multivesicular liposome.

U.S. Pat. No. 4,855,090 (Wallach) discloses multilamellar lipid vesicles (liposomes) having a high encapsulating mass and volume for hydrophilic or lipophilic materials. The lipophilic phase contains a surfactant (e.g. polyoxyethylene fatty ethers, polyoxyethylene cetyl ether, lauryl ether) with a sterol (e.g. cholesterol) and a charge producing amphiphile having a higher melting point than that of the surfactants. No biological data are given to indicate any efficacy of the claimed formulae in delivering peptides.

European Pat. Appl. No. 143,949 (Nakagama et al.) discloses a conventional liposome applying hydrogenated naturally occurring phospholipids to obtain a stable form of liposome. A fatty acid, preferably oleic acid at above 10 w % but preferably below 15 w % yields the most stable form of liposome capable of holding a drug within. Under these conditions, lecithin at its optimal weight percentage will form a lamellar liposome having oleic acid in the middle. However, at higher weight percentages of oleic acid, the phospholipids will form a micelle with oleic acid in the core, not a liposome. As disclosed by Wallach, Nakagama et al. applied cholesterol and tocopherol to strengthen the physical stability of the liposomal membrane, and applied negatively charged materials to achieve a slow releasing liposomal formulation within the body. After an intravenous infusion of liposomes containing 10,000 U of urokinase, a slow and sustained release of urokinase was observed in rabbits.

Both Wallach's and Nakagama et al.'s compositions are different from the compositions of the present invention. For example, both Wallach and Nakagama et al. have applied cholesterol, in combination with tocopherol and oleic acid, to strengthen liposomal membranes, and both have also applied a series of charged phospholipids, but neither have directly treated pharmaceutical agents such as peptides or drugs with, for example, phospholipids or cholesterol, although they have added surfactants.

In addition, in one embodiment of the present invention, microparticles comprising the pharmaceutically active agent urokinase (referred to herein as uPA) may be made by using glycerophosphorylcholine (referred to herein as GPC) and a water soluble cholesterol in the presence of a nonionic surfactant having an HLB value of above 15, and the microparticles are suspended in micelle in a fatty acid having a chain length of $C_{14}$ or less (referred to herein as MCT). A small amount of PC and/or PS may be added together with another nonionic surfactant (having an HLB value of less than 6). The liposomal uPA of Honda and Nakagama et al. is believed to be absorbed via alpha-glycerophosphate pathways which are involved in intramembranous syntheses of chylomicron, apoproteins, etc. and drained through the lymphatics. However, in the present invention, the uPA-containing microparticles in micelle (and not in liposome), for example, are believed to be (and preferably are) absorbed via the monoglyceride pathways (as is MCT) and channeled into the portal system.

U.S. Pat. No. 4,849,227 (Cho) disclosed a system in which a pharmaceutically active peptide was "pinned" into solid cholesterol granules in the presence of sodium lauryl sulfate, coated with a solution containing mono-, di-, or tri-glycerides and fatty acids; coated with water soluble materials, e.g. hydroxypropylcellulose, and enteriocoated. The resultant dried powder was packed into a hard gel capsule or made into a pressed tablet. The absorbed cholesterol-bound insulin was believed to form chylomicron in vivo. It was found to be bioavailable and bioactive in some diabetics: i.e. an oral insulin dosage between 0.33–0.74 U/kg (average 0.5U/Kg) effectively lowered blood sugar and increased serum insulin levels.

PCT Pat. Appl. PCT/GB91/00510 (Cho) discloses the oral delivery of peptides by the integration of peptides with specially selected, neutrally charged phospholipids and apo-proteins (e.g. apoprotein B48, AI, AII, etc.) or those known precursors of in vivo formation of such apoproteins (e.g. oleic acid, etc.). It is believed that membrane-integrating compounds are associated with the biologically active materials and integrated into forming the membrane system of chylomicron. Chylomicron forms a remnant chylomicron in the blood circulatory system, which is channeled into the liver. Thus, a peptide (e.g. insulin) bound with the membrane system of chylomicron may be channeled into the liver. Such a system is absorbed and forms part of a chylomicron, and is distinguishable from the disclosures of Wallach and Nakagama et al., in that neither Wallach nor Nakagama et al. are directed to formation of the membrane of remnant chylomicron.

The present invention, for use in oral insulin formulations and other applications, is significantly different from all the above-cited disclosures. For example, in cholesterol—and the phospholipid-bound insulin microparticles in micelle embodiment of this invention after oral or TuD administration, the composition is absorbed and predominantly channeled into the portal system and then the liver as well as systemic circulation.

In the above-cited disclosures, various lipids and/or surfactants are used to deliver (orally or otherwise) peptides/drugs through mechanisms of known or as yet unknown transmembranous absorptions. Such mechanisms may involve, e.g. liposomes, liposheres, lipoprotein-microparticles, lipid vesicles, and others, which are predominantly known to involve syntheses of chylomicron, apolipoproteins, lipoproteins or others within the absorptive membrane, and which are ultimately drained through the lymphatic vessels and thoracic duct. The overall absorption of such peptides/drugs by applying the above described formulations may be sporadic, erratic, unpredictable, and lacking uniformity in terms of bioavailability. This is expected from the characteristic physiological flow-kinetics of lymph fluids from the thoracic duct as the lymph fluid outflow from the thoracic duct is sporadic and not a uniform steady flow.

More particularly, PCT Patent Application PCT/GB91/00510 (Cho) discloses oral delivery systems for peptides, such as insulin, by dissolving the insulin into a hydrophilic solution, which contains a surfactant having an HLB value of 14 or above, and a lipophilic solution containing cholesterol:PC (at usually 6–8:1 ratio), apolipoproteins, 50 w/v % or more of oleic acid to hopefully enhance an in vivo syntheses of apoprotein, chylomicron, lipoproteins, etc. at the intestinal membrane, involving the glycerophosphate pathways. In the present invention, the water soluble-phospholipid bound microparticles are suspended in MCT micelle. However, the solutions of Cho (PCT/GB91/00510) were microfluidized and made into a microemulsion.

Gasco discloses formulations containing various drugs in solid lipid microspheres. More particularly, Gasco discloses a microemulsion prepared by contacting a molten lipid (which may contain a drug) with a mixture of water and surfactant heated to the lipid's melting temperature, and dispersing the microemulsion in water to create a lipid microsphere dispersion. It is believed, based upon the disclosure of Gasco, that such microspheres resemble a liposome described by Fabre, H. et al. in J. Phys. Chem. 85: 3493, (1981). Gasco also discloses lyophilization of the microsphere dispersion. However, it is believed that any freeze-drying or heating of an emulsion, microemulsion, liposphere, liposome, lipid vesicle, micelle, or solid emulsion (e.g. U.S. Pat. No. 4,849,227 (Cho)) will cause irreversible damage to the system and may deteriorate the bioactivities of the pharmaceutically active agents, especially peptides, glycoproteins, etc. Gasco does not disclose any biological data after applying the liposheres containing deoxycorticosterone, salbutamol, salmon calcitonin, somatostatin, and erythropoietin. It is believed that these compounds may be partially inactivated by heating together with the fatty acids applied by Gasco.

In addition, there are no related known disclosures relating to the embodiment of the present invention wherein trans-umbilico-dermal delivery of the compositions of this invention is employed. Other formulations and methods for delivery of drugs or peptides, although different than the present invention, are summarized as follows:

Liu, J. C. in Internat. J. Pharm. 44: 197 (1988) applied an iontophoresis of d.c. current of various wave form to facilitate and regulate the transdermal ("TD") delivery of insulin in rats. U.S. patent application Ser. Nos. 804661 and 899049, now U.S. Pat. No. 5,023,252 (Hsieh) disclose anhydrides and esters of macrocyclic lactone and ketones at 0.1–30 wt. % as a TD enhancer for a drug (e.g. triamcinolone acetonide). U.S. Pat. No. 4,649,075 (Jost) discloses a foam device which is a disk on a truncated inverted cone of macroporus cellular polymer core containing insulin, nonoxylnol-9, ocotoxynol, etc. and an outlayer containing a microporous cellular polymer. Makino, Y. et al. (Japan Pat. Appl. 84/182724) have used pyroglutamates as a dermal penetrating enhancer for TD delivery of indomethacin. PCT Publication No. WO 85/05036 (Weber, C. J. et al.) discloses the use of 33–50% DMSO and 2.5% of HPMC gel as a penetrating enhancer for TD delivery of insulin. M. Ferreira Mouta, Jr. (Braz. Pedido PI BR 84/1369 A) discloses mixed insulin with an oily excipient and incorporated with a plaster for TD delivery of insulin. Nagai, T. J. in Controlled Release 2:121 (1985) has incorporated triamcinolone with carbopol-934, a brand of carbomoer, and applied it on an adhesive layer of HPC for buccal mucosal delivery of insulin. German Pat. No. DE 3406497 (Franzky et al.) discloses dissolved isosorbide dinitrate in a mixture of polyethyleneglycol-glycerin partial ester with oleic acid, glycerin partial ester with capric and caprylic acids, isopropyl palmitate and water in the presence of a surfactant having an HLB value of 8 and cosurfactant having an HLB value below 8, and applied isosorbide for use as a trans-dermal (TD) system. Kazim, M. et al. in Surg. Forum 35: 64 (1984) has mixed insulin with the penetration enhancers DMSO and n-decylmethyl sulfoxide, and applied the mixture over the skin of streptocin-induced diabetic rats, covered it with a nonporous polyethylene patch, and observed antihyperglycemic effects in rats.

The above and other cited references have not made any disclosures of any compositions useful in transdermal applications of compositions which are similar to the compositions of the present invention. More particularly, the dermal areas on which these other TD formulations were applied are entirely different from the embodiment of the present invention which is specifically concerned with a trans-umbilico-dermal application of compositions of the present invention via falciform ligament and its anatomically associated system.

In the early 1980s, the Belmac firm of Tampa, Fla., developed a "navel drop" which consisted of camphor which was dropped into the navel foci, was absorbed through the falciform ligament and its related system into the mesenteric and portal vasculatures, induced a vasodilation and was supposed to have improved hemorrhoidal conditions in humans. Camphor, among other compounds, causes cutaneous vasodilation (Bowman, W. C. & Rand, M. J. in *Textbook of Pharmacology*, 2nd ed., p. 16.3 (1980)). Therefore, after dropping the navel drop (camphor) into a human navel, its being a cutaneous vasodilator, it is readily absorbed via the falciform ligament and its surroundings. However, an administration of any other TD forms of macromolecules or drugs, unlike the pure camphor, may not be readily absorbed through the falciform ligament. Such a TD formulation has to be modified specifically for the trans-umbilico-dermal delivery system. The trans-umbilico-dermal delivery system embodiment of the present invention and the "navel drop" containing camphor as its main component are thus entirely different, as the present invention relates to transdermal delivery formulations for pharmaceutically-active agents (e.g. peptides or drugs) which may be effectively administered via the falciform ligament.

The micelles of this invention, like compounds such as glycerol and fatty acids having a chain length of less than about $C_{14}$, monoglycerides, diglycerides, and the products of triglyceride hydrolysed by pancreatic lipase (e.g. 2-monoglycerides) are believed to be absorbed, via monoglyceride pathways, readily and rapidly from the cellular membrane by a passive diffusion mechanism, and are directed into the portal system. The absorption of relatively large and completed systems, as discussed by Larsen, K. et al. in Chem. Phys. Lipid, 12:321 (1980) or, e.g. an infinite periodic minimal surface (IPMS) as discussed by Longley, W. et al. in Nature 303:612 (1983) may be by a mechanism grossly similar to those involving pinocytosis or endocytosis. However, in such a mechanism the absorbed lipid apparently does not involve alpha-glycerophosphate pathways but rather the emonoglyceride path and is thereby channeled into the portal system. This is different from the known mechanism of absorption of fatty acids having a chain length of $C_{16}$ and above (referred to herein as LCT), emulsions, liposomes, lipid vesicles, liposphere, etc. which are absorbed via the alpha-glycerophosphate pathways at the membrane, are involved in syntheses of chylomicron, membranes for chylomicron, lipoproteins, apoproteins and others at the cell membrane, and are channeled through lymphatics into the thoracic duct. LCT are primarily absorbed from the cell membrane by pinocytoses or other as yet unknown mechanisms. An involvement of Pyer's patch at the small intestinal membrane, for the absorption of IPMS, liquid-crystalline phase of micelle, etc., is a plausible hypothesis. (Larson et al.; Longley et al.).

Without wishing to be bound by any one theory, it is believed that after the microparticles (containing a pharmaceutically active agent) in micelle of this invention are absorbed by the human body, they are channeled into the portal system. The formulation may contain one or more inhibitors for reticuloenthothelial system (RES) activity. The invention is capable of being passed through the absorptive columnar enterocytes, the Pyer's patch and others. The pharmaceutically active agent may thus be channeled into the portal system. When a fatty acid having a chain length of $C_{14}$ or less (referred to herein as MCT), a lysophospholipid (referred to herein as lyso-PL), and a fatty acid salt are added into the water, a lamellar L-alpha (lamellar or liquid crystalline) phase of the micelle is formed. At relatively high lipid concentration of the micelle, in the presence of phosphatidylcholine (PC), sphingomyelin, phosphatidyiserine (PS), etc., the spherical micelle is transformed into a rod shaped micelle. When the lipid concentration is increased further, especially in the presence of cardlollpin, phosphatidic acid (referred to herein as PA), a hexagonal lipid cylinder (liquid crystalline phase, or H1) is formed. It is possible to formulate, e.g. by using PC, a lamellar liquid crystalline phase with solvents other than water, such as ethylene glycol, and properly secreted surfactants. The spherical, rod-shaped, lamellar L-alpha or liquid crystalline phases may be obtained by simply altering the concentrations and the types of lipids used, by changing the temperature of solvents used, by selecting appropriate phospholipids, (referred to herein generally as PL), by changing the fluidity of protein-bound lipids, etc. These various phases involving the lipids-water (or other selected solvent) interactions, are generally known as micelle. (Larsson, K. et al. J. Colloid, Interface Sci. 72: 152, (1979); El-Nokaly, M. et al., J. Colloid Interface Sci. 84:228 (1981)).

A microemulsion is the reversed type of liquid phase of an ordinary L1 phase micelle. For example, water aggregates in a continuous hydrocarbon chain medium and water lamellae are separated by lipid bilayers (L2 phase) in aqueous systems of polar lipids and triglyceride oil. In the presence of, for example, lyso-phophatidylcholine (referred to herein as lyso-PC) it becomes a microemulsion. Liposomes are formed when water is added into the lamellar liquid-crystalline phase at above its swelling limit by gentle stirring. The lamellar liquid crystalline phase may consist of concentric lipid bilayers alternating with water layers. Sonicating the unilamellar aggregates under certain conditions may yield lipid vesicles. By further diluting the liposome, a so-called liposphere may be formed. The pharmacokinetic properties of a micelle, especially during its absorption from the cellular membrane and the transporting systems involved, are significantly different from that observed after introducing a pharmaceutically active agent within a liposome, microemulsion, lipid vesicle, liposphere, emulsion, or lipid suspension. (Ekwall, P., Advances in Liquid Crystals, Vol. 1, Chapter 1, Academic Press, N.Y. (1975)).

For example, in one embodiment of this invention, urokinase (referred to herein as uPA) is employed as the pharmaceutically active agent, the microparticles were made with specially prepared, water soluble cholesterol made in accordance with the method of Proksch et al. in Clin. Chem. 24/11:1924–26 (1978) (i.e. polyoxyethanyl-cholesteryl adipate, containing about 30% water soluble cholesterol and GPC, a water soluble enzymatically hydrolysed PC, i.e. sn-3-glycerophosphorylcholine, obtained after incuvating PC with its specific hydrolysing enzyme, phospholipidase-B, prepared by the method of Kates described in Techniques in Lipidology, Elsevier, Amsterdam (1972). The uPA in sodium phosphate buffer solution (pH 7.4) was bound with GPC:GPS (4:2-1 Mol ratio), and the water soluble cholesterol (4:2-1 Mol ratio of C:PC) in the presence of lyso-PC (i.e. sn-1-acyl-3-glycerophosphorylcholine, a lipid soluble end product of PC hydrolysed by phospholipidase-A2) and a nonionic surfactant (polyoxy-40-stearate), and made into microparticles in 15–20 v/v % of the final volume of MCT. The MCT contained another nonionic surfactant having an HLB value of less than 6. The MCT and above-described mixture were micronized to form uPA-containing microparticles suspended in MCT micelle. The overall bioavailability and bioactivity of the uPA-microparticles in MCT micelle was excellent. In addition, assaying for uPA from serum/plasma samples and for uPA microparticles in MCT-micelle, in vitro, using the ELISA method, was found to be easier when uPA was bound to GPC/GPS-water soluble cholesterol, as compared with when uPA was 'bridge-locked' with PC, PA apoproteins cholesterol, etc., as disclosed for example in PCT/GB91/00510 (Cho), and Chung, K. H., Chung, J. S. & Cho, Y. W.: Presented at 13th Congress International Soc. Thrombosis & Homeostasis, Jul. 3, 1991, Utrecht. discussed above. The stability of this embodiment of the invention was good; however, it was further stabilized by adding less than 5 w/v % of LCT into the MCT-micelle, and by adding a small quantity of PC and PS, into the MCT solution.

In another embodiment of this invention, the pharmaceutically active agent is quinine which is contained within microparticles suspended in the MCT micelle. After oral or TuD administration and absorption, it is targeted to erythrocytes and hepatacytes hosting plasmodium malarial parasites which may utilize the components therein (i.e. microparticles containing quinine which are suspended in micelle to repair the damaged membrane of erythrocytes and hepatocytes. Also, microparticles containing vincristin have been successfully targeted to experimental IgM Immunocytoma cells in Wister rat and introperitoneally inoculated P388 mouse leukemic cells.

In one particularly, preferred embodiment, water soluble cholesterol is added as a sterol, to stabilize the microparticles in MCT micelle. Optionally, an LCT (i.e. having a chain length of $C_{16}$ or higher, preferably $C_{18}$ such as 1; 9-octadecenoic) may be added to the MCT micelle (at a concentration of 5 w/v % or less of the final MCT-micelle) to augment and stabilize the MCT-micelle. After adding properly selected surfactants to the LCT at or above the critical-micelle-concentration (CMC) (but preferably at or below 5 w/v %), a second micelle (i.e. LCT micelle) is formed. This LCT-micelle is compatible with the MCT-micelle containing the microparticles.

The objects and features of the present invention will be apparent from the following detailed description and the claims.

SUMMARY OF THE INVENTION

The present invention relates to pharmaceutical compositions comprising microparticles suspended in micelle in at least one fatty acid having a chain length of $C_{14}$ or less. The microparticles comprise at least one pharmaceutically-active agent, at least one water soluble or miscible phospholipid, at least one lipid soluble or miscible phospholipid, at least one non-ionic surfactant having an HLB value of about 15 or greater, at least one non-ionic surfactant having an HLB value of about 6 or less, and at least one water soluble or miscible sterol. In a particularly preferred embodiment, the lipid soluble phospholipid is an enzymatically hydrolyzed phospholipid lipid soluble end product, i.e. a lysophospholipid. The pharmaceutical composition may additionally comprise at least one long chain fatty acid having a chain length of $C_{16}$ or greater, present in a concentration of no greater than about 5 w/v % based upon the total composition.

The present invention also relates to a method of preparing the above-descried pharmaceutical composition comprising: (a) admixing at least one pharmaceutically-active agent with at least one water soluble or miscible phospholipid, at least one lipid soluble or miscible phospholipid, at least one non-ionic surfactant having an HLB value of about 15 or greater, at least one non-ionic surfactant having an HLB value of about 6 or less, and at least one water soluble or miscible sterol and micronizing the admixture to form microparticles; and (b) suspending the microparticles in at least one fatty acid having a chain length of $C_{14}$ or less to form microparticles in micelle. The microparticles in micelle may thereafter optionally be admixed with at least one long chain fatty acid having a chain length of $C_{16}$ or greater, which is present in a concentration of no greater than about 5 w/v % based upon the total composition.

The present invention also relates to a method of trans-umbilico-dermal administration of a pharmaceutical composition to a patient, which comprises contacting the dermal area of a patients' navel with the above-described pharmaceutical compositions. The present invention also relates to the use of such compositions for treatment of diabetes, administration of antibiotic therapy, treatment of hypertension, cancer or chemotherapy treatment, administration of hormonal therapy, administration of antiparasitic therapy, and for targeting delivery of the pharmaceutical composition to a specific organ.

DETAILED DESCRIPTION OF THE INVENTION

Figure 1:
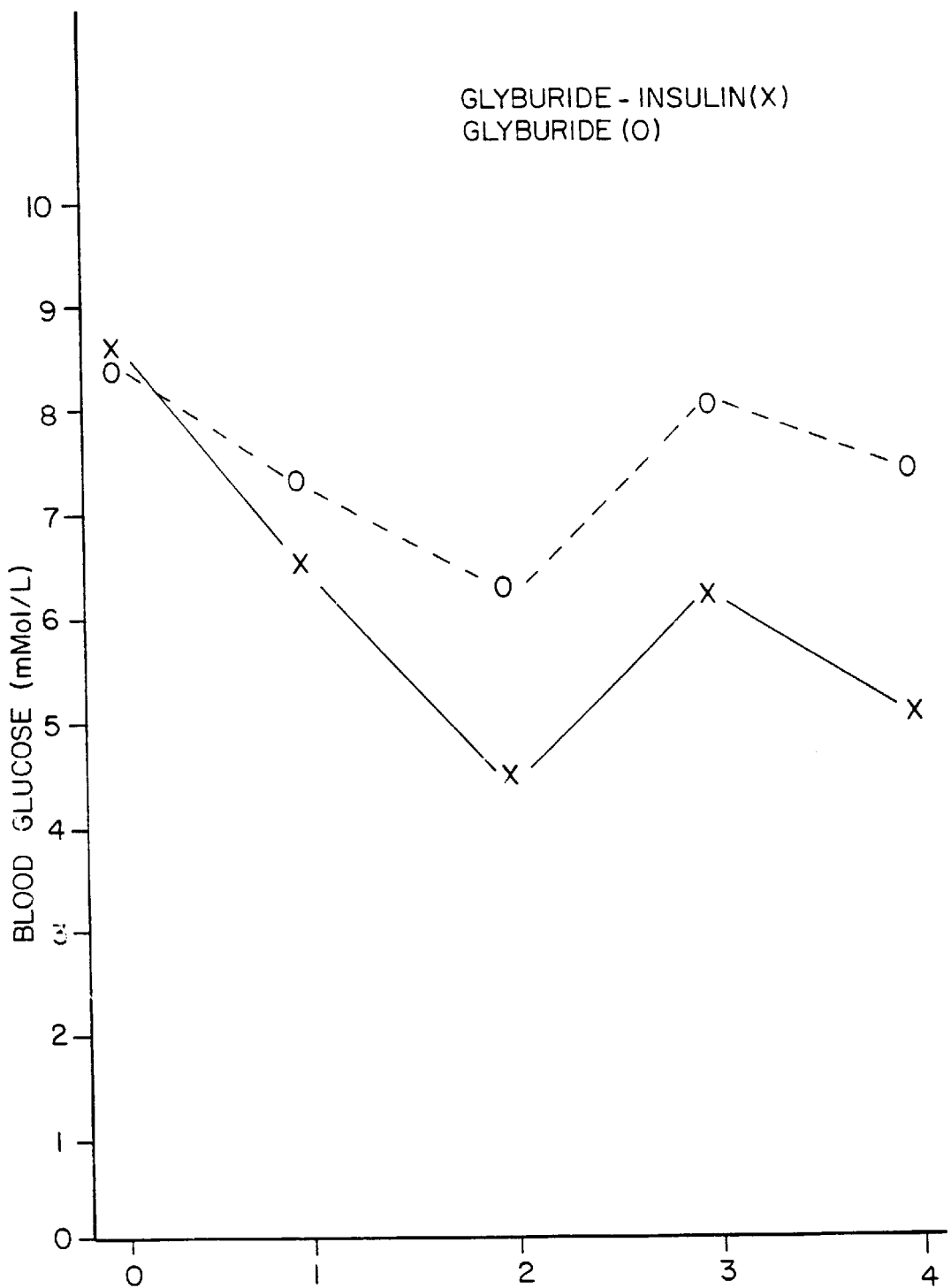
FIG. 1 illustrates blood glucose levels obtained after oral administration of glyburide plus insulin in accordance with this invention compared to levels obtained after oral administration of glyburide alone in glyburide-resisting NIDDM patients.

The pharmaceutical composition of this invention contains microparticles suspended in micelle in at least one fatty acid having a chain length of $C_{14}$ or less (referred to herein as MCT). The microparticles contain one or more pharmaceutically-active agents which may be peptides, drugs or nutritional food products which have enhanced bioavailability and activity after the oral, rectal, trans-umbilico-dermal, buccal, sublingual, intranasal, intrapulmonic, or ocular administration of such a composition. Such formulations may be applied for targeting the composition as a slow, controlled-release formulation for special organs or tissues, and may be given orally, parenterally, intrathecally (for delivering into the brain and the spinal cord areas), transdermally, or by other means. The pH for the pharmaceutically-active agents may be adjusted to the optimal pH, in vitro, for the pharmaceutical agent or agents employed. As used in this specification and in the appended claims, "micelle" refers to the high degree of association of microparticles in solution typically observed, for example, with respect to molecules or ions of many surfactants, as described for example in Vol. 4 of the Encyclopedia of Chemical Technology (R. Kirk and D. Othmer, eds. (1954)), pp. 939–40. Thus the microparticles in the present invention are highly associated when suspended in the $C_{14}$ or less fatty acid. As used in this specification and the appended claims, the term "fatty acid" means monobasic organic acids of chain length $C_1$ or greater, as set forth, for example, at page 281 of the Von Nostrand Chemist's Dictionary (1953). In this specification and the appended claims, "fatty acid" may be further modified by specifying a specific chain length.

The microparticles are suspended in micelle in at least one fatty acid having a chain length of $C_{14}$ or less, preferably $C_{12}$ or less. Such fatty acids include formic, propionic, butyric, valeric, caproic, caprylic, capric, lauric and myristic acid and mixtures thereof.

In preparing the microparticles of this invention which are then suspended in MCT micelle, the pharmaceutically-active agent is made relatively stable, and is noncovalently and reversibly bound with at least one water soluble or miscible phospholipid, without degradation of the pharmaceutical agent.

While not wishing to be bound by any one theory, it is believed that noncovalent bonds between the agent (e.g. a peptide) and the phospholipid which may stabilize peptide structure are ionic bonds, hydrogen bonds, hydrophobic interactions, and the Van der Waals interaction. A lipid such as a phospholipid may strongly bind with a peptide at various radical groups of the peptide, such as at carboxyl, sulfonyl, hydroxyl, amino, and ammonial radicals, and lipids may form esters or ethers with the peptide. This type of binding should be avoided. Bile salts, for example, are strongly charged and may change the properties of a peptide, and thus should not be employed as a surfactant in this invention.

The pharmaceutically-active agents which may be employed in the present invention include, but are not limited to: (1) peptides such as insulin, growth hormones, interferon, calcitonins, urokinase, coagulation Factor-VIII, coagulation Factor IX, erythropoietin; (2) compounds having poor bioavailability and/or compounds for targeted delivery to specific organs or systems, such as nafcillin, vincristin, cephazoline, doxorubicin, quinine, chloroquine, primaquine, d-alpha-tocopherol (which is also an antioxidant), and gentamicin; (3) compounds which, after absorption, are predominantly bound to plasma proteins and/or rapidly biotransformed at the liver, thereby exhibiting poor bioactivity, such as glyburide, indomethacin, oxyphenbutazone, chlorothiazle, propranolol, cyclophosphamide; and (4) those neuropharmacologics which mimic sustained intravenous infusion of compounds, preferably those capable of crossing the blood-brain-barrier membrane, such as physostigmine, fluoxetine, and feldene. As will be apparent to those skilled in the art, the choice of agent or agents employed is dependent upon the condition, disease or illness being treated, or the therapy to be employed. In a particular preferred embodiment, the peptide is insulin, and the composition is employed for the treatment of diabetes. In another particularly preferred embodiment, the agent is vincristin, and the composition is employed in cancer treatment.

As used in this specification and the appended claims, the term "water soluble or miscible phopholipid" refers to phospholipids (referred to herein generally as PL) and phospholipid derivatives which are water soluble or miscible, either alone or in the presence of a suitable nonionic surfactant or surfactants, or a suitable hydrolyzing enzyme. For example, phospholipids which are capable of water solubility or miscibility in the presence of suitable surfactants and/or hydrolyzing enzymes include diacylglycerols, phosphatidylcholines (PC), phosphotidylethanolamines (PE) (which are zwitterionic), phosphatidylserines (PS), phosphatidylglycerols (PG), phosphatidylinositol (PI), diphosphatidyl glycerol (DPG), and phosphatidic acid (PA). Other water soluble or miscible phospholipids which may be employed in the present invention include, but are not limited to, glycerophospholipids such as glycerophosphates (GP) (e.g. sn-1- and sn-3 glycerophosphate), glycerophosphorylcholines (GPC), glycerophosphorylethanolamines (GPE) (e.g. sn-3-glycerophosphorylethanolamine), cholines, phosphorylcholines, phosphorylethanolamines, ethanolamines, glycerophosphorylserines (GPS) (e.g. sn-3-glycerophosphorylserine), glycerophosphorylglycerols (GPG) (e.g. sn-3-glycerophosphorylglycerol), and mixtures thereof.

Water soluble or miscible phospholipid derivatives suitable for use include water soluble or miscible enzymatic hydrolysis end products of phospholipids. As used in this specification and the appended claims, "water soluble or miscible enzymatic hydrolysis end products of phospholipids" refers to water soluble or miscible end products obtained after incubating a specific phospholipid with its specific hydrolyzing enzyme to obtain such an end product. For example, phosphatidylcholine (PC) may be enzymatically hydrolyzed by incubating with the enzyme phospholipase-B to yield water soluble glycerophosphorylcholine (GPC). A particularly preferred embodiment of GPC is sn-3-glycerophosphorylcholine. Similarly, phosphorylglycerol (PG) may be enzymatically hydrolyzed by incubating with the enzyme phospholipase-B to yield water soluble glycerophosphoryglycerol (referred to herein as GPG). A particularly preferred embodiment of GPG is sn-3-glycerophosphorylglycerol. Such enzymatic hydrolysis end products may be prepared by the method disclosed in M. Kates, Techniques in Lipidology (Elsevier, Amsterdam 1972) (incorporated herein by reference), and are well known to those skilled in the art.

Alternatively, water soluble GPC may be prepared from egg yolk lecithin by applying selective alcoholysis with methanolic tetrabutylammonium hydroxide solution according to a modified version of the method of H. Brockerhoff and M. Yurkowski in Canadian J. Biochem. 43:1777 (1965) (incorporated herein by reference).

As used in this specification and the appended claims, the term "lipid soluble or miscible phospholipid" refers to phospholipids and phospholipid derivatives which are lipid soluble or miscible, either alone or in the presence of a suitable surfactant or surfactants, or a suitable hydrolyzing enzyme. In a particularly preferred embodiment, the lipid soluble or miscible phospholipid derivatives suitable for use are lipid soluble or miscible enzymatic hydrolysis end products of phospholipids. These end products are referred to herein as lysophospholipids, or lyso-PL. As used in this specification and the appended claims, "lipid soluble or miscible enzymatic hydrolysis end products of phospholipids" refers to lipid soluble or miscible end products obtained after incubating a specific phospholipid with its specific hydrolyzing enzyme to obtain such an end product. For example, phosphatidylcholine (PC) may be enzymatically hydrolyzed by incubating with the enzyme phospholipidase-A2 to yield lipid soluble lyso-PC (i.e. sn-1-acyl-3-glycerophosphorylcholine). Such enzymatic hydrolysis end products may be prepared by the method of Kates, referenced above and are well known to those skilled in the art. Lipid soluble enzymatic hydrolysis end products particularly preferred for use as in this invention are exemplified by those set forth in the following table, together with the corresponding base phospholipid (PL) and enzyme employed to product the enzymatic hydrolysis end product or lyso-PL:

| Base Phospholipid (PL) | Enzyme | Lipid Soluble enzymatically hydrolyzed end product (referred to generically as lyso-PL) |
|---|---|---|
| Phosphatidylcholine (PC) | Phospholipase-A2 | sn-1-acyl-3-glycerophosphorylcholine (lyso-PC) |
| | Phospholipase-C | sn-1,2-diacylglycerol |
| | Phospholipase-D | sn-1,2-diacyl-3-glycerophosphate |
| Phosphatidylglycerol (PG) | Phospholipase-A2 | sn-1-acryl-3-glycerylphosphorylglycerol (lyso-PG) |
| | Phospholipase-C | sn-1,2-diacylglycerol |
| | Phospholipase-D | sn-1,2-diacylglycerolphosphate |
| Phosphatidic Acid (PA) | Phospholipase-A2 | sn-1-acyl-3-glycerophosphate (lyso-PA) |
| | Phosphatase | sn-1,2-diacylglycerol |
| Phosphatidylethanolamine (PE) | Phospholipidase-A2 | sn-1-acyl-3-glycerophophoryl ethanolamine (lyso-PE) |
| | Phospholipase-C | sn-1,2-diacylglycerol |
| | Phospholipase-D | sn-1,2-diacyl-3-glycerophosphate |
| Phosphatidylserine (PS) | Phospholipase-A2 | sn-1-acyl-3-glycerophophorylserine (lyso-PS) |
| | Phospholipase-D | sn-1,2-diacyl-3-glycerophosphate |

Other lipid soluble or miscible phospholipid enzymatic hydrolysis end products suitable for use include, for example: 1-Myristoyl-sn-glycero-3-phosphocholine; 1-Myristoyl-sn-glycero-3-phosphoethanolamine; 1-Myristoyl-sn-glycero-3-phospho-(N,N-dimethyl)-ethanolamine; 1-Palmitoyl-sn-glycero-3-phosphocholine (or ethanolamine); 1-Palmitoyl-rac-glycero-3-phosphocholine; 1-Palmiltoyl-sn-glycero-3-phospho-(N,N-dimethyl)-ethanolamine; 1-Stearoyl-sn-glycero-3-phosphocholine, and mixtures thereof.

More than one water soluble or miscible phospholipid may be used in the preparation of the microparticles. For example, in one preferred embodiment, the pharmaceutically active agent may be bound to, for example, GPC and/or GPS by being mixed and incubated with, e.g., lyso-PC, while gently stirred at 25° C. in a water bath.

The microparticles may also additionally comprise at least one lipid substrate compound selected from the group consisting of phosphatic acid, phosphatidylcholine, phosphotidylethanolamine, and phosphatidylserine and phosphatidylglycerol, and mixtures thereof. Such lipid substrates may aid in stabilizing the MCT micelle composition of this invention.

Other lipid soluble materials which may be employed in conjunction with the lysophospholipids include 1-Oleyl-2-acetyl-sn-glycerol, 1,2-Dioctanoyl-sn-glycerol, 1,2-Didecanoyl-sn-glycerol, etc.; some of the 1,2-Diacyl-phospholipids may include 1,2-Dioleoyl-sn-glycero-3-phosphocholine, 1,2-Dimyristoyl-sn-glycero-3-phosphocholine, 1,2-dimyristoyl-rac-glycero-3-phosphocholine, 1,2-Dimyristoyl-sn-glycero-phosphoethanolamine, 1,2-Dimyristoyl-sn-glycero-3-phosphatidic acid (Na), 1,2-Dipalmitoyl-sn-glycero-3-phosphocholine, 1,2-Dipalmitoyl-sn-glycero-3-phosphoethanolamine, 1,2-Distearoyl-sn-glycero-3-phosphatidic acid (Na), and mixtures thereof.

At least one water soluble or miscible sterol is also present and is incorporated into of the phospholipid while maintaining the structure of the phospholipid and of the surfactant at an optimal concentration to increase its adherence to absorptive cells and to supplement the surfactant activity in vivo. The sterols for use preferably include cholesterol, cholesterol esters, cholesteryl-17-bromohepta-decanoate, cholesteryl octonoate, cholesteryl oleate, cholesteryl palmitate, cholesteryl sulfate, cholesterol monohydrate, and mixtures thereof. Such sterols may be made into water soluble form, e.g. polyoxyethanyl-cholestryl adipate, which has been solubilized as an L-alpha-phase of a lipid-water system; or at least made into a water miscible sterol by utilizing various surfactants. This invention employs an application of the water soluble or miscible sterol, wherein it is used in conjunction together with of one or more enzymatically hydrolyzed and water soluble phospholipids such as GPC or GPS, and enzymatically hydrolysed end products of lipid soluble materials such as lyso-PC.

The pharmaceutically-active agent (e.g. insulin or glyburide), is admixed with at least one non-ionic hydrophilic surfactant having a HLB (hydrophile/lipophile balance) value of 15 or greater, preferably above 16, and at least one nonionic lipophilic surfactant having an HLB value of 6 or below, preferably 5 or below, with each dissolved in a proper solvent. If necessary, the pH is adjusted, and transport enhancers and/or protease inhibitors are added.

The surfactants which may be employed in this invention are preferably non-ionic surfactants, which are well known to those skilled in the art. Surfactants having HLB value of about 6 or less include, but are not limited to substituted sorbitan compounds, substituted glyceryl compounds, and substituted polyoxyethylene compounds having from 1–100 oxyethylene moieties, preferably including sorbitan-monocaprylate, sorbitan-monopalmitate, sorbitan-monostearate, sorbitan-sesquistearate, sorbitan-trioleate, sorbitan-monooleate, sorbitan-sesquioleate, sorbitan dioleate, glyceryl-monosterate, glyceryl-monoleate, glycerol-dioleate, decaglyceryl-monostearate, decaglyceryl-pentastearate, decaglyceryl-monolinolate, decaglyceryl-monolaurate, and decaglyceryl-monomyristate.

Surfactants suitable for use having an HLB value of 15 or greater include polyoxyethylenes and their derivatives having from 1–100 oxygen moieties, such as polyoxyethylene-lauryl ether, polyoxyethylene-hydrogenated castor oil, polyoxyethylene-sorbitan monooleate, polyoxyethylene-monostearate, and polyoxyethylene-lauryl ether. The surfactants should be carefully selected to avoid suppression of the bioactivities of the pharmaceutically-active agents employed. It will be understood that the applicable surfactants are not to be limited to those named above but may include other surfactants, including emulsifiers.

In one preferred embodiment, the pharmaceutically active agent Factor-VIII is combined with 4–1:1 Mol ratio concentrations of GPC and GPS prepared as disclosed by M. Kates. In the presence of a water soluble cholesterol (polyethoxyethanyl-cholesteryl-adipate prepared by the method of Proksch & Bondeman), lyso PC at less than 0.005 mMol, aprotinin, and a surfactant having an HLB value of above 15, such as polyoxy 40-stearate in phosphate buffer. This solution is added and mixed into MCT solution having an HLB value less than 6 (e.g. glyceromonooleate), and micronized at room temperature by using a modified Nanmizer (the Freund Industrial Co., Tokyo) or a Microfluidizer (the Microfluidics Co., Newton, Mass.).

Just prior to administration of the above-described composition, about 5 w/v % or less, preferably less than about 4.5 w/v % (of the final product) of a solution containing LCT, a nonionic surfactant having an HLB value less than 6 and an antioxidant, may be added to the composition and micronized at room temperature, which may further stabilize the MCT-micelle. Occasionally, a small amount of PC:PA (about a 2–4:1 Mol ratio) may be included into the MCT so as to further stabilize the MCT-micelle. The microparticles mixed with MCT (and optionally LCT) water, oil, and the lamellar L-alpha-phase of micelle may exist in equilibrium. (Rydhag. L. et al., J. Am. Oil Chem. Soc. 58:830 (1981)).

The long chain fatty acids (LCT) in which the microparticles suspended in MCT micelle may be further admixed or suspended has a chain length of $C_{16}$ or greater. In one preferred embodiment, the LCT has a chain length of $C_{18}$ or greater and at least one unsaturated bond. In a particularly preferred embodiment, such acids include 4- or 9-tetradecenoic, 9-hexadecanoic, 6-,9-, or 11-octadenoic acid, 9-, or 12-octadecadienoic, 9-, 12-, 15-, 11-, or 13-octadecatrienoic, 9-, 11-, 13-, or 15-octadecatetraenoic, 9-eicosenioic, 5-, 8-, 11- or 14-eicosatetraenoic, 13-docosenoic, or 15-tetracosenoic acid or combinations thereof. The long chain fatty acid may also contain 20–50 v/v % of glycero-monooleate, -dioleate, and/or -trioleate. By adding up to 5 w/v % of the LCT to microparticles suspended in MCT micelle, the microparticles suspended in MCT micelle may be further stabilized. In one optional particularly preferred embodiment, the LCT and additional nonionic surfactant having an HLB value of 6 or below (as previously described) may be added to the microparticles suspended in MCT micelle.

The pharmokinetic behavior of pharmaceutical compositions of this invention wherein 5 w/v % or less LCT is added to the microparticles in MCT micelle differs significantly from products containing say greater than 10 w/v % LCT (e.g. oleic acid). At the latter LCT concentrations, the pharmaceutically active agent would be in liposome or liquid sphere form, not in micelle in accordance with this invention. Accordingly, a composition containing greater than 10 w/v % LCT requires the active pharmaceutical agent contained therein to be absorbed via pinocytosis, etc. and/or forming chylomicron, etc., which involves alpha-glycerophosphate pathways, channeling through the lymphatic system, and drained through the thoracic duct in a sporadic, non-uniform way. When the optional LCT concentration is 5 w/v % or less, as in one embodiment of this invention, the MCT micelle is stabilized without effecting the pharmokinetic, absorptive behavior of the MCT micelle and its associated pharmaceutically active agent. Additionally, a small amount of phospholipids and a nonionic, lipophilic surfactant having an HLB value of 6 or less may be added (together with the LCT) to the microparticles in MCT micelle, to further stabilize the composition.

This invention also relates to a method of trans-umbilico-dermal (TuD) administration of the pharmaceutical composition of this invention to a patient. The pharmaceutical composition is applied on the skin area of the human navel, the falciform ligament (paraumbilical veins) and its related system. This pharmaceutical TuD delivery system may be applied, for example, in the following settings: (1) for targeting a cancer chemotherapeutic, e.g. doxorubicin, into the liver, uterus, ovary, lung, stomach, rectum, colon, etc.; (2) for delivering an antimalarial drug, e.g. quinine, into plasmodium parasite-containing red cells and hepatocytes; and (3) for administering a cholinesterase inhibitor, e.g. physostigmine, through the blood-brain barrier into CNS systems and improving the cognitive functions of patients suffering from the Alzheimer's Disease, etc. An enhancer for the trans-umbilico-dermal adsorption of such TuD formulations, may be added. These may include, but are not limited to, dimethyl formamide, propylene glycol, diethyl-m-toluane, salicylate, and other adsorption enhancers, at concentrations well known to those skilled in the art.

In accordance with this invention, when a pharmaceutically active agent residing in microparticles suspended in micelle was administered from the umbilical foci and channeled into the mesenteric circulatory system and portal system, thus directing the microparticles into the liver, the overall pharmacological actions of the microparticles was found to be similar to that of the results of slow, intravenous infusion of the same pharmaceutically active agent. Thus, this TuD administration of, e.g. physostigmine, was found to have induced grossly similar activities as compared with results obtained after its intravenous injection. This is useful, for example, in improving the cognitive functions of patients suffering from Alzheimer's Disease. In addition, insulin delivered via the TuD system was found to cause increased serum insulin and decreased blood sugar in diabetic patients, grossly similar to the responses observed after slow intravenous infusion of insulin. The TuD embodiment of this invention includes applying compositions of this invention dropwise onto the navel, patched over the navel, or made into a "cream-type" formulation and spread over the navel of human patients.

For the trans-umbilico-dermal ("TuD") delivery of a pharmaceutically-active agent such as a peptide (e.g. insulin) or of a drug (e.g. glyburide), the compositions of the present invention should be absorbed through the thin layer of non-fatty scar tissue; and once the formulations are absorbed into the mesenterics, the macrophageal systems and their activities have to be retarded. It has been found that a trans-umbilico-dermal administration of insulin in accordance with the present invention was as effective as that of a parenterally injected regular insulin in diabetics. Furthermore, in accordance with this invention, insulin may be dissolved in, e.g., ethanol, in the presence of a group of enhancers for transdermal penetration, e.g. hydrophilic/lipophilic surfactants, propyleneglycol, dimethylformamide, diethyl-m-toluamide, salicylates, etc., and made into stable microparticles with a group of water soluble glycerophospholipids in the presence of an optimal concentration of tris galactoside-terminated-cholesterol and lyso-PC in MCT.

Inhibitors for the macrophageal and for the protease activities may also be added into the micro-particle compositions. More particularly, inhibitors for the macrophargeal system (e.g. mucopolysaccharolproteins or mucopolysaccharolipids, nonulosaminic acid, sialic acid) and protease inhibitors (e.g. aprotinin) may also be added to the microparticles.

The invented compositions, which include bound bioactive agents (wherein the efficacy of such agents is known to be activated by their intrahepatic biotransformations) may be targeted for specific organs such as the liver. The bioactivity of such compounds can be enhanced while the systemic, toxic and side effects of the compounds are reduced (e.g. phenacetin is biotransformed into acetoaminophen).

The microparticles may also additionally comprise at least one antioxidant compound. In one preferred embodiment, the antioxidant employed may be d-alpha-tocopherol.

In a preferred embodiment, the composition of this invention is capable of slow, controlled release and of being targeted at high dosage to the liver or other organs. The above-mentioned inhibitors of macrophageal activities, for example, sialic acid, may be replaced with, for example, one or more activator compounds. In a preferred embodiment, substituted cholesterols such as triantennary galactose-terminated cholesterols, most preferably N-(tris-beta-D-galactopyranosyloxymethyl-methyl)-N-(4-5-cholesten-3-beta-oxyloxysuccinyl)glycinamide, or an ultramicronized polyvinylpyrrolidone such as polyvinyl alcohol, or similar compounds may be employed as activators.

In another preferred embodiment, by simply eliminating the inhibitors for macrophageal activity from the composition, it is believed that the pharmaceutically-active agent in microparticle suspended in micelle will be carried into the portal veins and will be channeled predominately to the liver.

The microparticles are prepared by micronizing the above-described admixture of pharmaceutically-active agent phospholipids, surfactants and sterol. As used in this specification and the appended claims, the term "micronized" refers to the method of reducing solid or liquid particles in size by subjecting them to shear forces, using techniques, procedures and equipment well known to those skilled in the art. The microparticle sizes of the composition of this invention preferably have an average diameter in the range of 0.01–0.15 $\mu$m. For example, when the composition comprises urokinase (uPA) as the pharmaceutically active agent in MCT micelle, the microparticle size is typically between 30–90 nm (within an average less than 60 nm); when the agent is insulin, it is typically 0.01–0.07 $\mu$m (with an average in the range of 36 nm).

The micelle may also be converted into a dried powder by spray coating the solution over a group of inert chemicals, e.g. carboxymethylcellulose, alginate, etc. The powder may then be packed into a hard gelatin capsule or pressed into a tablet form. As used in this specification and the appended claims, the term "inert chemicals" refers to chemicals or compounds which are not usually absorbed from the gastrointestinal system after its oral intake, but instead are eliminated as feces. Accordingly, such inert chemicals lack appreciable systemic effect after intake.

The invention is exemplified by, but not limited to, the following examples.

EXAMPLE 1

An oral insulin formulation having an enhanced bioavailability and activity, and which mimics the properties of endogenously secreted insulin, which is primarily channeled into the liver, has been made and one of the representative formulations is summarized as follows:

To make a final volume of about 300 ml, a sufficient quantity of bovine insulin (about 55 mg, provided that one mg of such insulin powder/crystalline has an activity of about 20 IU) to yield about 16 IU per 5 ml of the final product or per 125 mg of the formulation contained in microcapsules, was dissolved in 95% ethanol (final volume made up to 75 ml) containing about 2,200 KIU of aprotinin and adjusted to about pH 2.8 by adding a saturated citric acid solution. To 25 ml of 95% ethanol, about 0.85–12.5, say 10.3 gm of glycerophosphorylcholine (GPC), about 4.1–6.3, say 5.2 gm of glycerophosphorylserine (GPS), 12.8–16.5, say 14.3 gm of water soluble cholesterol, about 750–918, say 850 mg of lyso-PC, and about 2.2–2.8, say 2.5 gm of polyoxy-40-stearate were added, and (in order of the above listing) gently and slowly dissolved at about 35°–40° C. in a water bath. To about 150 ml of MCT, about 4.6–6.8 say 5.5 gm of glycerolmonooleate was added and dissolved, at about 35°–40° C. in a water bath. These two solutions were gently mixed, homogenized, and the volume was made up to about 280 ml by adding MCT, and micronized by using either the Nanomizer or Microfluidizer (of the Microfluidics Co. of Newton, Mass.) at room temperature. The yield MCT-micelle containing insulin in the microparticles was kept in a dark, brown glass container and stored in a dark cool place at a temperature between 2°–8° C., but not permitted to freeze.

To about 3.5–5.0, say 4.7 w/v % of the final volume of product, glyceromonooleate at about 2–6, say 4 v/v % of the final volume of oleic acid applied, and about 1.0–2.5, say 1.8 gm d-alpha-tocopherol were added, mixed, homogenized and passed 2–4 times through the Microfluidizer at a shear force of 10,000 psi. A proper quantity of antimicrobials, such as about 1.5 gm sodium benzoate and about 1.5–3.8, say 2.0 mg of nonulosaminic acid may be added into the above oleic acid solution. Just prior to its administration to human subjects, the microparticles suspended in MCT-solution micelle and the oleic acid (i.e. LCT) solution may be mixed and made up to 300 ml with additional MCT. Each 5 ml of the final product may contain about 14–20, say 16 IU of bovine insulin.

Alternatively, the above oleic acid solution may be slowly homogenized in the MCT solution and after the final volume is made up to 300 ml with additional MCT, micronized for 5–10 min in cold by using a Nanomizer (or passed through the Microfluidizer for 4–6 passes) at room temperature.

EXAMPLE 1A

The final product of Example 1 may be spray-coated over inert materials. Such inert materials include, for example, calcium-carboxymethylcellulose (CMC-Ca), hydroxypropyl cellulose (HPC) gelatin, etc. The dried product may be packed into a hard gelatin capsule or made into a pressed tablet. A Spir-A-Flow (Mini Model) of Fruend Industrial Co. of Tokyo may be applied. The Spir-A-Flow is an improved fluidizer-coater.

In order to further preserve the chemical and pharmacological activities as well as the stability of the final product, it was made into microcapsules (having a mean diameter of about 0.5–1.5 say 0.75 mmO) as follows:

The final product was spray coated with COCONADE (a commercial product of coconut oil of Kao Soap Co., Tokyo) and gelatin in its liquid form. Both COCONADE and gelatin, in a beaker in water bath, were heated at 40°–70° C., and 50°–90° C., respectively. The cool, final product solution and two heated coating solutions were sprayed at a rate of 15–20 ml/min for the product, 10–16 ml/min for COCONADE, and 25–40 ml/min for the gelatin solution, through the triple nozzles of the Spherex TRN (a product of Freund Industrial Co., Tokyo) into a slowly rotating (with respect to its longitudinal axis) round glass chamber-column of a length of about 1.5 m and having a diameter of 20 cm at the descending part of its U-shaped tube.

Briefly, the two U-shaped tubes are connected in such manner as to make a pressed S-shaped tube: i.e. the first part of the descending part of U-tube, having a diameter of about 20 cm and length of about 1.5M is attached (and funneled) to the ascending part of a length about 2M long, having a diameter of about 12 cm, which is further attached to the descending part of the upside down U-tube having a length of about 1M and a diameter of about 12 CM. The outflow opening of the upside down U-tube was attached to the collecting sheave, collecting the microcapsules (less than 0.3 mm in diameter) and cold vegetable oil was pumped into the U-tube, and recirculated through the U-tube, starting from the top of larger descending part of U-tube with the input opening for the flowing vegetable oil, and was directed to the narrow, ascending part of the U-tube, connected to another descending part of the narrow U-tube. Another extremely cold vegetable oil at temperatures of about 0°–(−5)°C. was circulated around the pressed S-shaped tube.

As the microparticles in micelle and heated droplets of the COCONADE and the gelatin solutions impacted the cold oil in the rotating glass chamber-column, microcapsules were formed containing the microparticles at the middle, coated by the COCONADE, and the outermost coating shielded by the hardened gelatin, with sizes ranging between 0.5–1.5 mm. The microcapsules were dried (at room temperature) and packed into hard gelatinous capsules (i.e. each 125 mg capsule to contain about 16 IU of bovine insulin). The insulin within the microcapsules in the hard gelatinous capsules was found stable for the six months of study period.

EXAMPLE 2

An glyburide-containing composition of the present invention, useful as an oral anti-hyperglycemic, may be made and representative formulations are summarized as follows:

| Chemicals | Quantity (per 400 Ml) | |
| --- | --- | --- |
| | Broad | Preferred |
| Part-I | | |
| Glyburide | 0.06–2.0 | 2.0 |

|  | Mg/Capsule | Mg/Capsule |
|---|---|---|
| Cholesterol | 3.9–15.6 Gm | 7.8 Gm |
| GPC | 7.0–28.0 Gm | 14.0 Gm |
| Lyso-PC | 1.4–13.8 Mg | 1.6 Mg |
| Ethanol (95% in water) | 40–250 Gm | 65 Gm |
| Polyoxyethylene 40 stearate | 0.05–20%+ | 5%+ |
| Part-II |  |  |
| MCT oil Make up to the final volume of | 350–450 Ml | 400 Ml |
| Nonulosaminic acid | 0.005–2.0 Mg | 0.05 Mg |
| Sorbitan trioleate | 5–30%++ | 25%++ |
| Part-III |  |  |
| Oleic acid | 0.5–5 w/v % of Part-I/II | 4.5 w/v % |
| Glycerolmonooleate | 0.5–15% v/v % of Oleate | 4.0 v/v % |
| d-alpha-tocopherol | 0.5–2.5 Gm | 1.2 Gm |
| (above quantity is per 400 Ml of the final composition) |  |  |

+(w/V % of the Part I solution)
++(w/v % of the Part II solution)

Glyburide powder is micronized with a Jet Mill (made by the Fruend Industrial Co. of Tokyo), and dissolved in ethanol in the presence of polyoxyethylene-40-stearate at room temperature, a water soluble cholesterol, and GPC. Lysophosphatidylcholine (lyso-PC) is dissolved in MCT in the presence of sorbitan trioleate and nonulosaminic acid. Both solutions are slowly mixed and passed through the nanomizer at a shear force of above 10,000 psi and cooled. To the resultant solution, 5 w/v % or less of an LCT (oleic acid) containing glycerolmonooleate and d-alpha-tocopherol are added, and re-micronized at above 10,000 psi with cooling at four to five passes. The final volume of the resultant solution is made up to 400 ml with MCT, and passed once through the microfluidizer.

The glyburide-containing composition may be made into microcapsule formulations using the Spherex TRN, or made into a powder using the Spir-A-Flow, or stored in a dark brown glass bottle at cool temperature (as in Example 1). If microcapsules are made (as, for example, in Example 1A), each microcapsule or hard gelatin capsule containing the powder preferably has about 0.5 mg active glyburide per 5 ml or 125 mg of the microcapsules.

EXAMPLE 3

An insulin-containing composition of the present invention may be prepared as in Example 1 above. After carefully blending and mixing glyburide together with one or more inert chemicals, e.g. HPC, CMC-Ca, alginate, or gelatin, the mixed powders are placed into the chamber of the Spir-A-Flow and dried at 27°–29° C. The insulin-containing solution of Example 1 is then spray coated over the inert chemical mixture. The dried powder of insulin plus glyburide-composition is packed into #1 sized capsules, with each capsule containing 8 units of insulin, and 0.5 mg of glyburide.

In the alternative, the insulin-containing composition of Example 1 and the glyburide-containing composition of Example 2 are mixed in such manner as to yield 8 units of insulin and 0.5 mg of glyburide per capsule, and the mixed solutions are spray coated over the inert chemicals by using the Spir-A-Flow; or the mixed solutions may be packed into soft gelatine capsules and may thereafter be orally administered.

EXAMPLE 4

Urokinase (uPA) available from Novabiochem Ltd. and having a makeup of 90% high molecular weight (i.e. about 54,000) and 10% low molecular weight (i.e. about 33,000) is dissolved in a sodium phosphate buffer solution having a pH of about 7.4, and mixed with about 0.05–2, preferably 0.5 mg GPC and 0.05–2, preferably 0.5 mg of GPA, in a water bath at a temperature of 37°–38° C. Lyso-PC is then added in amounts of 0.005–0.1, preferably 0.04 mg, in the presence of 800–17,600, preferably about 888 KIU of aprotinin, and polyoxy-40-stearate, with the stearate present in amounts of 0.05–5, preferably 1.2 v/v % (of the final volume of hydrophilic phase) at room temperature; 0.9–3.6, preferably 1.4 mg of water soluble cholesterol; and 1.8–9.0, preferably 1.4 mg of PC are dissolved in about half of the final volume of MCT used in the presence of sorbitan trioleate, present in amounts of 0.01–4, preferably 0.5% of the final volume of lipophilic phase. The above hydrophilic and lipophilic solutions are mixed, homogenized and passed through a microfludizer (for example, manufactured by Microfludics Co. of Newton, Mass.), at a shear force of 60,000–80,000 psi with cooling for 2–3 min.; 0.15–15, preferably 0.8 v/v % glyceromonooleate/oleic acid solution and 0.5–2.5, 0.88 mg d-alpha-tocopherol are added to oleic acid solution, which is present in amounts of 0.5–5.0, preferably 4.5 w/v % of the final volume of the above lipophilic & hydrophilic phase solutions and then made up to a total volume of 20 ml by adding MCT, and micronized again at a shear force of 6,000–8,000 psi with cooling for another 2–3 minutes. The yield solution may be stored in a dark brown bottle at 2°–40° C. Alternatively, the resultant solution may be made into microcapsules by conventional means, for example using the Spherex TRS as described above.

EXAMPLE 5

18,000–24,000, say 20,000 KIU aprotinin is added to 1.6–2.0 say 1.8 gm of bovine insulin and dissolved, adjusting its pH to about 2.2–3.0, say 2.4 by adding saturated sodium citrate solution). About 0.2 mM calcium chloride, 8.6–12.3, say 10.7 gm of water soluble cholesterol, about 5.9–8.6 say 7.6 gm of GPC, about 2.2–5.2, say 3.9 gm of GPS, about 0.6–1.2, say 0.8Mg of lyso-PC, and about 4.6–7.8, say 6.0 gm of polyoxy-40-stearate are dissolved in about 50 ml of ethanol. About 0.2–0.9, say 0.4 gm of Hydroxypropylcellulose (HPC) is slowly but properly dissolved at room temperature in 10 ml of deionized water. All of the above solutions are mixed, and its final volume is made up to 70 ml by adding ethanol, mixing and homogenizing. Ten ml of 0.9% physiological solution, as a commercial form of TRASYLOL-TM, contained 100,000 KIU of aprotinin (Bayer).

PC, ranging from 0.1–1.2 preferably 0.25 gm, is dissolved in 10 ml of MCT oil. The above mixture is added to the PC-containing MCT solution and homogenized. To this MCT solution, d-alpha-tocopherol (preferably at 2.5–4.8, say 3 v/v % of the final volume of products) is mixed and its final volume is made up to 100 ml by adding 50% of an MCT:ethanol solution (ethanol, 99% is used). The admixed solutions are homogenized and ultramicronized by using the Nanomizer. Sodium salicylate at concentration of 0.04–0.12 mg, say 0.08 mg per 5 ml of the final product, dissolved in glycerol (1:4 solution) is added to the final product and homogenized.

The above TuD-Insulin solution contains about 14–20, say 16 IU of bovine insulin per drop. Usually one to three (preferably 2) drops of TuD-Insulin is placed on the navel. About 20–24, say 22 drops of the TuD-insulin is one ml.

EXAMPLE 6

Trans-Umbilico-Dermal Drug Delivery System (For Physostiamine)

For cognitive therapy, physostigmine infusion may improve transitory cognitive functions, while ergoloid mesylates (e.g. Hydergine-TM) may improve the subjective cognitive functions. An intermittent dosing of fluoxetine, thioridazine, diphenhydramine, and other neuropharmacologics in combination may improve the noncognitive behavioral symptoms. Most of these drugs can be effectively given orally. However, physostigmine must be parenterally given to be effective. Physostigmine salicylate injection (USP) is available (pH 4–6; 90–110.0% solution); 0.5–1.0 mg repeated per 0.5–1.0 hour-intervals (for management of over dosage of Anticholinergia or post anesthesia).

A TuD formulation for physostigmine has been designed. TuD-physostigmine may eliminate for the need of frequent intravenous or intramuscular injections.

Physostigmine, to make 0.06–0.12 mg, preferably 0.1 mg per drop, is added into GPC (0.8–3.0; preferably 0.8 gm), lyso-PC (0.55–10; preferably 6 mg), polyoxy-40-stearate (3.2–24.4; preferably 12.2 gm) in MCT (5–8 gm). After homogenizing the solution, sodium salicylate (0.04–0.12; preferably 0.08 mg dissolved in 1:4 glycerol per 5 ml of the final product) is added. It is made up to 40 gm with MCT, made up to the final volume of 50 gm with 99% ethanol, rapidly homogenized, and micronized at cold temperature. If possible, physostigmine and its contained TuD formulation should not be exposed to light. It should be stored in a dark glass, at cool temperature. An antioxidant (d-alpha-tocopherol, about 0.5% of the final product) may also be added.

EXAMPLE I

Clinical Study

Two IDDM and 3 NIDDM patients, 4 males and 1 female, aged between 42–59 years old, were studied. After overnight fasting, at 6:00 a.m. of the study day, 32 u of insulin as in Example 1A were orally given and the blood sugar as well as serum insulin level were measured hourly for 3 hours (under fasted conditions). The results are set forth below:

| Pt. # | Age & Sex | Class | Blood Sugar (mMol/L) | | | | Serum Insulin (uU/ml) | | | |
|---|---|---|---|---|---|---|---|---|---|---|
| | | | 0 | 1 | 2 | 3 | 0 | 1 | 2 | 3 |
| EXAMPLE 1 - INSULIN in MICROCAPSULE (32 Units) | | | | | | | | | | |
| 1 | 59M | NIDDM | 11.2 | 9.5 | 7.0 | 6.2 | 20 | 60 | 73 | 56 |
| 2 | 54M | NIDDM | 10.4 | 8.3 | 7.9 | 6.5 | 26 | 41 | 64 | — |
| 4 | 46M | NIDDM | 9.8 | 9.2 | 8.5 | 5.9 | 27 | 64 | 72 | 40 |
| 5 | 42M | IDDM | 12.7 | 12.0 | 9.2 | 7.9 | 11 | 16 | 47 | 29 |
| 6 | 43M | IDDM | 10.9 | 9.8 | 8.3 | 6.6 | 14 | 21 | 52 | 50 |
| Mean | 48.8 | | 11.0 | 9.8 | 8.2 | 6.6 | 19.6 | 40.4 | 61.6 | 43.8 |

Therapeutically significant reduction in the blood glucose levels were observed after the administration of microcapsule-insulin compositions of the present invention prepared in accordance with Example 1A, with the maximum effects observed at 3 hours after the dosing, and a gentle elevation in the serum insulin level, peaking at 2 hours after the medication, was also observed. The microparticle-bound insulin suspended in MCT micelle composition of this invention was thus shown as an effective oral formulation for lowering the blood sugar while moderately elevating the serum insulin in diabetic patients.

EXAMPLES II & III

Clinical Studies

A group of NIDDM, who were previously known as non-responsive to oral glyburide (or other oral hypoglycemic agents) and were receiving parenteral injections of insulin as well, were selected and studied after overnight fasting. On the early morning of the Study Day-1, the NIDDM patients were orally given the insulin-containing (32 Units) and glyburide-containing composition (2.0 mg) of Example 3. The blood sugar levels were measured at times 0, 1, 2, 3, and 4 hours after the medication, and the serum insulin levels were measured by a radio immunoassay method from the blood samples collected at times 0, 1.5 and 3.0 hours of the study. After one day of washout period, on the Study Day-3, a study similar to those of the Study Day-1 was repeated after an oral administration of the glyburide-containing composition (2.0 mg) of Example 2 above.

Figure 2:
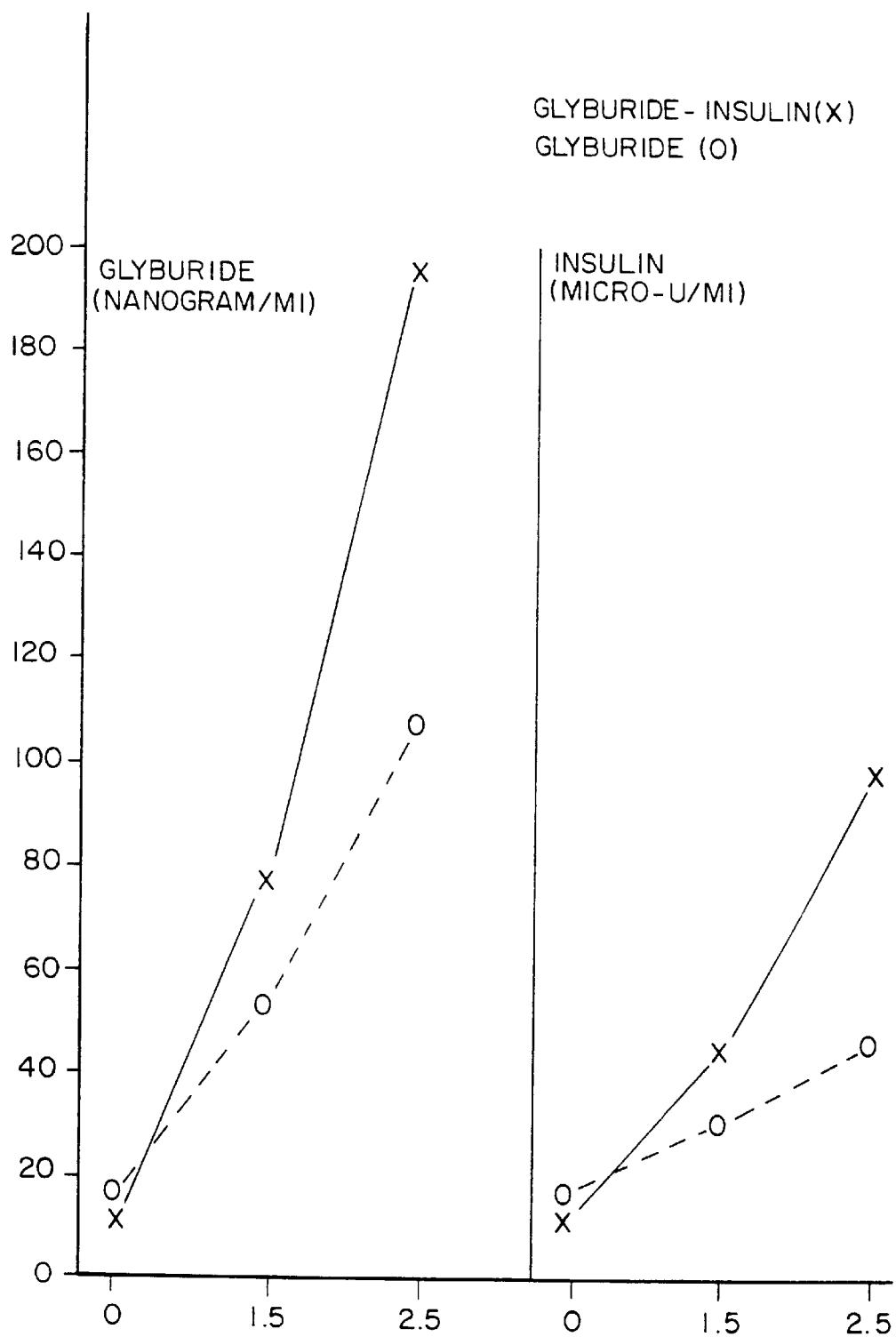
FIG. 2 illustrates serum glyburide and serum insulin concentrations obtained after oral administration of glyburide plus insulin in accordance with this invention compared to levels obtained after oral administration glyburide alone in accordance with this invention in glyburide-resisting NIDDM patients.

In these glyburide-resisting NIDDM patients, the glyburide-containing composition (Example 2) caused a marked reduction in the blood sugar level, modified 2-hour post-prandial blood sugar levels, moderately elevated serum glyburide and insulin levels (see FIG. 1), while after the insulin-containing plus glyburide-containing (Example 3) composition, a significant antihyperglycemic effect normalizing the 2-hour post-prandial blood sugar levels, marked elevation in the serum glyburide level and significant elevation in the serum insulin levels were observed (as shown in FIG. 2). A combination of the insulin-containing and the glyburide-containing compositions thus restored the activities of glyburide in these glyburide-resisting NIDDM patients, as would be the case with parenteral injections of insulin.

EXAMPLE IV

Clinical Study

A group of healthy volunteers participated in this study. After an overnight fasting, about 34,000 U of a composition of this invention comprising uPA as the pharmaceutically-active agent prepared as described in Example 4 was given orally at 10-minute intervals for three consecutive doses (a total of 102,000 U of the uPA-containing composition) for 3 consecutive days, while plasma levels of uPA (measured by ELISA assay and FDP agglutination test) were measured and compared against the effects observed after intravenously infusing 50,000 U of uPA in the same subjects. The uPA was infused over 150 minutes on Day-1, Day-2, and Day-3 of the study.

FDP assay was used as an indicator for the bioactivity of uPA. Detection and semi-quantitative analyses of fibrinogen degradation products (FDP) was accomplished by agglutination of latex particles coated with specific antibodies (from Diagnostica Stago of France). Enzyme immunoassay for the detection of human urokinase (uPA) antigen in plasma was based on the double antibody principle, using two different monoclonal antibodies by the ELISA method (American Diagnostics, U.S.A.).

As shown below, 100,000 U (34,000 U given every 10 min for three times) of the uPA-containing composition of this invention (Example 4), orally given for 3 consecutive days, was bioavailable and bioactive, and achieved better results in terms of effects observed than the corresponding treatment of 50,000 U of uPA infused for 3 consecutive days in the same subjects.

ELISA ANALYSIS AND FIBRIN DEGRADATION PRODUCTS (FDP) AGGLUTINATION TEST OF PLASMA SAMPLES AFTER ORAL AND INTRAVENOUS uPA IN VOLUNTEERS (N = 4 Males)

| Hours | 0 | 6 | 12 | 24 | 32 | 48 | 54 |
|---|---|---|---|---|---|---|---|
| ELISA ANALYSIS (Units = O.D. at 405 × 1/10) | | | | | | | |
| EXAMPLE-4-uPA (102,000 IU on Time-0, Time-24, and Time-48) | | | | | | | |
| Mean | 32 | 68 | 58 | 66 | 64 | 66 | 69 |
| Intravenous Infusion of uPA (50,000 IU on Time-0, Time-24, and Time 48) | | | | | | | |
| Mean | 35 | 54 | 38 | 34 | 62 | 31 | 59 |
| FDP AGGLUTINATION TEST (Graded as +1, +2, and +3; Readings × 1/10) | | | | | | | |
| EXAMPLE-4-uPA (102,000 IU on Time-0, Time-24, and Time-48) | | | | | | | |
| Mean | 6 | 20 | 25 | 18 | 27 | 20 | 27 |
| Intravenous Infusion of uPA (50,000 IU on Time-0, Time-24, and Time-48) | | | | | | | |
| Mean | 6 | 16 | 10 | 6 | 18 | 13 | 22 |

***the Grades for the FDP Agglutination Test are SCORED as 0, 0.25 (read as 0.3), 0.5, 0.75, (read as 0.8), 1.0, 1.25 (read as 1.3), 1.5, 1.75 (read as 1.8), 2.0, 2.25 (read as 2.3), 2.5, 2.75 (read as 2.8), and 3.0

EXAMPLE V

Clinical Study of the Trans-Umbilico-Dermal Delivery of Insulin in Diabetics Five male diabetics, 2 IDDM and 3 NIDDM, of ages between 28–56 (mean of 43.6) years old participated in the study. After an overnight fasting, and after measuring the blood glucose and serum insulin levels at Time-0, 2 drops (about 32 U) of insulin of the insulin-containing composition of the present invention prepared as described in Example 6 was applied, i.e. dripped on the patients' navel, and the blood sugar and serum insulin levels were measured, hourly, for 2 to 3 hours.

As shown in the table below, the blood glucose level of about 10.3 mMol/L at Time-0 was decreased to about 7.5 mMol/L within one hour, and was reduced further to 5.5 mMol/L at Time-3 hours. A correspondingly high serum level of insulin was also observed. Thus, the insulin-containing composition of Example 5 has been demonstrated to be an effective and bioavailable therapeutic agent in diabetics when employed via trans-umbilical-dermal administration: i.e., the onset of action was faster than that of an oral administration of the insulin-containing composition of this invention as in Example 1.

TRANS-UMBILICAL-DERMAL ADMINISTRATION

| Case | Age & Sex | Class | Body Weight Kg | 0 | 1 | 2 | 3 | (Hrs) |
|---|---|---|---|---|---|---|---|---|
| | | | | Blood Glucose (m/ML) | | | | |
| | | | | Serum Insulin-uU/ml | | | | |
| 1 | 28M | IDDM | 54 | 9.8 | 5.6 | 7.0 | 5.8 | |
| 2 | 33M | IDDM | 48 | 10.2 | 8.5 | 6.8 | 4.8 | |
| 3 | 56M | NIDDM | 65 | 9.8 | 6.9 | 5.6 | 5.0 | |
| 4 | 52M | NIDDM | 79 | 11.0 | 8.3 | 7.2 | 6.0 | |
| 5 | 49M | NIDDM | 62 | 10.5 | 8.0 | 6.9 | 5.7 | |
| Mean | 43.6 | | 61.6 | 10.3 | 7.5 | 6.7 | 5.5 | |
| | | | | Serum Insulin uU/ml | | | | |
| 1 | | | | 14 | 66 | 73 | 43 | |
| 2 | | | | 19 | 71 | 61 | 60 | |
| 3 | | | | 28 | 96 | 78 | 48 | |
| 4 | | | | — | 92 | 82 | 72 | |
| 5 | | | | 22 | 78 | 60 | 66 | |
| Mean | | | | 20.8 | 80.6 | 70.8 | 57.8 | |

EXAMPLE VI

Augmented Targeted Delivery of Cancer Chemotherapeutics

Based on the Goldie-Goldman's hypothesis, a permanent drug resistance may occur in tumor cells as a result of random genetic mutations at a rate of, say, one in 1 million cells. In a minimally detectable size of tumor having about 1,000 million cells, it may already have formed one or more resistance cell lines. Thus, multidrug regimens are useful in overcoming resistance by the cancer cells to a chemotherapeutic agent, and it is important to initiate the combination drug therapy as early as possible. Furthermore, it is important to saturate the cancer cells with the known effective chemotherapeutic agents in combination, while reducing any undesirable side effects.

The compositions of this invention, comprising various pharmaceutically-active agents, are believed to be useful in augmenting the therapeutic indices of some of the well known cancer chemotherapeutics, whose toxic or severe side effects are well known and documented.

In one embodiment, vincristin-containing formulations of this invention for parenteral or trans-umbilico-dermal administration in cancerous patients may be made in accordance with the method of this invention as follows: ten mg of vincristin, admixed in 1 gram of manitol, 13 mg of methylparaben, and 2 mg propylparaben in acetic acid/sodium acetate containing water to make 10 ml, with a pH of 3.5–5.5 was prepared. This mixture was added and dissolved into 0.5 mg GPS, 1.4 mg GPC, 0.8 mg lyso-PC, 1.5 mg of water soluble cholesterol, and 2.2 mg polyoxy-40-stearate, and the resultant mixture was micronized at room temperature. 5 grams of glyceromonooleate dissolved in MCT and the above vincristin-containing solution were admixed. A sufficient quantity was added of the vincristin solution and MCT to yield about 0.5 mg of vincristin per ml of the final product, and the final solution was microfluidized at room temperature and filtered. This composition may be administered paraneterally, trans-umbilico-dermally, or orally.

The vincristin-containing composition of this invention, as described above, in an intraperitoneal injection, was found effective in prolonging the survival times in the P388 mouse leukemia model. The P388 mouse leukemia model was prepared according to the method described by Daoud and Juliano in Cancer Res. 48: 5518 (1986). Female mice were intraperitoneally inoculated with P388 mouse leukemia (1 million cells/0.1 ml) on Study Day-0. The study drugs were intraperitoneally injected on Study Day-1. The mortality was monitored daily, and the mean survival times of mice treated with vincristin (1.25 mg/kg), mice treated with the vincristin-containing composition of this invention (1.25 mg/kg) (referred to as the Targeted Drug Delivery System or TDDS) vs. the control group receiving 0.1 ml/10 g of 0.9% NaCl solution, were studied. The results were as follows:

| MEAN SURVIVAL TIME OF TREATED VS. CONTROLLED LEUKEMIC MICE | | |
|---|---|---|
| Group | Mean | SEM |
| Control | 14.6 | 2.9 (days) |
| Vincristin (1.25 mg/kg) | 21.2 | 4.1 |
| TDDS-Vincristin | 42.0 | 6.8 |

For the tumor model, a group of Wister rats were inoculated subcutaneously with 100,000 IgM immunocytoma cells in 0.5 ml of plain RPMI 1640 medium (from the Grand Island Biological Co.), and when the tumor diameter was about 20 mm or more in size within 6 days, the rats were used for the study. Reduction in the size of tumor mass for both treated and control rats, as % changes in the tumor size were measured, and summarized as follows:

| REDUCTION IN TUMOR VOLUME IN RATS (%) | | |
|---|---|---|
| | Vincristin | TDDS-Vincristin |
| Conc. | 1.25 mg/kg | 1.25 mg/kg |
| Mean | 11.5 | 34.7 |
| SEM | 8.6 | 10.3 |

As demonstrated above, the vincristin-containing composition of this invention apparently was preferentially absorbed by the tumor and leukemic cells of experimentally induced cancerous rats and leukemic mice. The therapeutic efficacy of vincristin was significantly increased by its use as a pharmaceutically active agent in the TDDS embodiment of this invention.

The compositions of this invention may be used to treat a number of conditions or in various therapeutic regimens. For example, in one preferred embodiment, the compositions of this invention may be employed in a method of treating diabetes. In another preferred embodiment, such compositions may be used in a method of antibiotic therapy. In yet another embodiment, such compositions may be employed in methods of cancer treatment or chemotherapy. In yet another embodiment, such compositions may be employed in hormonal or antiparasitic agent therapy.

It should be understood that various changes and modifications to the preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A pharmaceutical composition prepared by the process comprising (a) admixing about 0.15–5 mg/l of at least one pharmaceutically-active agent, about 17.5–70 g/l of at least one phospholipid selected from the group consisting of glycerophosphates, glycerophosphorylcholines, phosphorylcholines, glycerophosphorylethanolamines, phosphorylethanolamines, glycerophosporylserines, and glycerophosphorylglycerols, about 3.5–34.5 mg/l of at least one phospholipid selected from the group consisting of sn-1-acyl-3-glycerophosphate, sn-1,2-diacylglycerol, sn-1-acyl-3-glycerophosphorylcholine, sn-1-diacyl-3-glycerophosphate, sn-1-diacyl-3-glycerophosphorylethanolamine, sn-1-,2-acyl-3-glycerophosphorylserine, sn-1,2-acyl-3-glycerophosphate, sn-1-acyl-3-glycerophosphoryl-glycerol, sn-1,2-diacylglycerophosphate, 1-myristoyl-sn-glycero-3-phosphocholine, 1-myristoyl-sn-glycero-3-phosphoetharnolarnine, 1-myristoyl-sn-glycero-3-phospho-(N,N-dimethyl)-ethanolarnine, 1-palmltoyl-sn-glycero-3-phosphocholine, 1-palmitoyl-rac-glycero-3-phosphocholine, 1-palmltoyl-sn-glycero-3-phospho-(N,N-dimethyl)-ethanolamine, 1-stearoyl-sn-glycero-3-phosphocholine, and mixtures thereof, about 0.05–20 w/v % of at least one non-ionic surfactant having an HLB value of about 15 or greater which is a polyoxyethylene compound having from 1–100 oxyethylene moieties selected from the group consisting of polyoxyethylene-lauryl ether, polyoxyethylene-hydrogenated castor oil, polyoxyethylene-sorbitan monooleate, polyoxyethylene-monostearate, and polyoxyethylene-lauryl ether, about 0.5–5 w/v % of at least one non-ionic surfactant having an HLB value of about 6 or less selected from the group consisting of sorbitan-monocaprylate, sorbitan-monopalimitate, sorbitan-monostcaratc, sorbitan-sesquisterate, sorbitan-trioleate, sorbitan-monooleate, sorbitan-sesquioleate, sorbitan-dioleate, glyceryl-monostearate, glyceryl-monoleate, glycerol-dioleate, decaglyceryl-monstearate, decaglyceryl-pentastearate, decaglyceryl-monlinolate, decaglyceryl-monolaurate, and decaglyceryl-monomyristate, and about 9.75–39 g/l of at least one sterol selected from the group consisting of polyoxyethanyl-cholesterol adipate, cholesterol, cholesterol esters, cholesteryl-17-bromoheptadecanoate, cholesterol oleate, cholesterol palmitate, cholesterol sulfate, cholesterol monohydrate, and mixtures thereof, and micronizing the admixture to form microparticles; and (b) suspending the microparticles in at least one fatty acid having a chain length of $C_1$ to $C_{14}$, thereby permitting the microparticles to associate to form micelles suspended in the fatty acid.

2. A composition according to claim 1, in which the pharmaceutically-active agent is selected from the group consisting of, insulin peptides, glyburide, growth hormones, interferon, calcitonins, urokinase, coagulation Factor-VIII, coagulation Factor IX, erythropoietin, indomethacin, nafcillin, gentamicin, vincristin, cephazoline, doxorubicin, d-alpha-tocopherol, oxyphenbutazone, chlorothiazle, propranolol, physostigmine, cyclophosphamide, quinine, chloroquine, primaquine, fluoxetine and feldene.

3. A composition according to claim 1, in which the microparticles additionally contain at least one lipid substrate compound selected from the group consisting of phosphatic acids, phosphatidylcholines, phosphotidylethanolamines, phosphatidylserines, phosphatidylglycerols, and mixtures thereof.

4. A composition according to claim 1, in which the sterol is polyoxyethylene-cholesterol adipate.

5. A composition according to claim 1, in which the sterol is water-soluble, or water miscible in the presence of a surfactant.

6. A composition according to claim 1 in which the microparticles additionally comprise at least one protease inhibitor selected from the group consisting of aprotinin and mucopolysaccharide extracted from egg white.

7. A composition according to claim 1, in which the microparticles additionally comprise a macrophageal activity inhibitor which is sialic acid.

8. A composition according to claim 1, in which the microparticles additionally comprise at least one activator compound for macrophageal or protease deactivation.

9. A composition according to claim 8, in which the activator compound is selected from the group consisting of polyvinyl alcohol and N-(tris-beta-D-galactopyranosyloxymethyl-methyl)-N-(4-5-cholesten-3-beta-oxyloxysuccinyl) glycinamide.

10. A composition according to claim 1, in which the microparticles additionally comprise at least one antioxidant.

11. A composition according to claim 10, in which the antioxidant is d-alpha-tocopherol.

12. A composition according to claim 1, in which the microparticles additionally comprise a macrophageal activity inhibitor which is nonulosaminic acid.

13. A composition according to claim 1, in which the microparticles in micelle are dried to powder form and packed into a gelatinous capsule for oral administration.

14. A method of preparing a pharmaceutical composition comprising:

(a) admixing about 0.15–5 mg/l of at least one pharmaceutically-active agent with about 17.5–70 g/l of at least one phospholipid selected from the group consisting of glycerophosphates, glycerophosphorylcholines, phosphorylcholines, glycerophosphorylethanolamines, phosphorylethanolamines, glycerophosphorylserine, and glycerophosphorylglycerols, about 3.5–34.5 mg/l of at least one phospholipid selected from the group consisting of sn-1-acyl-3-glycerophosphate, sn-1,2-diacylglycerol, sn-1-acyl-3-glycerophosphoryl-choline, sn-1-diacyl-3-glycerophosphate, sn-1-diacyl-3-glycerophosphorylethanolamine, sn-1-,2-acyl-3-glycerophosphorylserine, sn-1,2-acyl-3-glycerophosphate, sn-1-acyl-3-glycerophosphoryl-glycerol, sn-1,2-diacylglycerophosphate, 1-myristoyl-sn-glycero-3-phosphocholine, 1-myristoyl-sn-glycero-3-phosphoethanolamine, 1-myristoyl-sn-glycero-3-phospho-(N,N-dimethyl)-ethanolamine, 1-palmiltoyl-sn-glycero-3-phosphocholine, 1-palmitoyl-rac-glycero-3-phosphocholine, 1-palmiltoyl-sn-glycero-3-phospho-(N,N-dimethyl)-ethanolamine, 1-stearoyl-sn-glycero-3-phosphocholine, and mixtures thereof, about 0.05–20 w/v % of at least one non-ionic surfactant having an HLB value of about 15 or greater which is a polyoxyethylene compound and derivatives thereof having from 1–100 oxyethylene moieties, about 0.5–5 w/v % of at least one non-ionic surfactant having an HLB value of about 6 or less selected from the group consisting of sorbitan-monocapiylate, sorbitan-monopalimitate, sorbitan-monostearate, sorbitan-sesquisterate, sorbitan-trioleate, sorbitan-monooleate, sorbitan-sesquioleate, sorbitan-dioleate, glyceryl-monostearate, glyceryl-monoleate, glycerol-dioleate, decaglyceryl-monstearate, decaglyceryl-pentastearate, decaglyceryl-monlinolate, decaglyceryl-monolaurate, and decaglyceryl-monomyristate, and about 9.75–39 g/l of at least one selected from the group consisting of polyoxyethylene-cholesterol adipate, cholesteryl cholesteryl esters, cholesteryl-17-bromohepta-decanoate, cholesterol oleate, cholesterol palmitate, cholesterol sulfate, cholesterol monohydrate, and mixtures thereof, and micronizing the admixture to form microparticles; and (b) suspending the microparticles in at least one fatty acid having a chain length of $C_1$ to $C_{14}$ to form microparticles associated to form micelles.

15. A method of trans-umbilico-dermal administration of a pharmaceutical composition to a patient, comprising contacting the dermal area of a patient's navel with the pharmaceutical composition of claim 1.

* * * * *

UNITED STATES PATENT AND TRADEMARK OFFICE
CERTIFICATE OF CORRECTION

Page 1 of 3

PATENT NO. : 5,858,398
DATED : January 12, 1999
INVENTOR(S) : Young W. Cho

It is certified that error appears in the above-indentified patent and that said Letters Patent is hereby corrected as shown below:

ABSTRACT: "about or less" should read –about 6 or less--.

Col. 10, line 26: "GPC," should read --(GPC),--.

Col. 13, line 28: "phopholipid" should read --phospholipid--.

Col. 13, line 35: "phosphotidyle-" should read --phosphatidyle- --.

Col. 14, Table: "glycerophophoryl" should read --glycerophosphoryl--.

Col. 15, line 36: "into of the" should read --into the--.

Col. 16, line 5: glyceryl-monoleate," should read --glyceryl-monooleate,--.

Col. 16, line 52: "tetradecenoic," should read --tetradecanoic, --.

Col. 16, line 56: "13-dococenoic should read --13-docosenoic--.

Col. 16, line 58: "v/v%" should read --w/v%--.

Col. 18, line 48: "predominately" should read --predominantly--.

Col. 19, line 44: "4 v/v%" should read --4 w/v%--.

Col. 20, Table: "Ml" (all occurrences) should read -- ml --; "Mg" (all occurrences should read -- mg --; "Gm" (all occurrences) should read -- gm --; "w/V%" (single occurrence) should read ---- w/v% --; and "v/v%" should read -- w/v% -- .

Col. 22, line 37: "0.8Mg" should read -- 0.8 mg --.

Col. 23, Table: "54M" should read --54F--.

UNITED STATES PATENT AND TRADEMARK OFFICE
CERTIFICATE OF CORRECTION

Page 2 of 3

PATENT NO. : 5,858,398
DATED : January 12, 1999
INVENTOR(S) : Young W. Cho

It is certified that error appears in the above-indentified patent and that said Letters Patent is hereby corrected as shown below:

Col. 23, Table: "(mMol/L)" should read -- (m/Mol/1) --.

Col. 23, line 47: "(mMol/L" should read --mMol/1--.

Col. 25, line 48: "mMol/L" should read --mMol/1--.

Col. 25, line 49: "mMol/L" should read --mMol/1--.

Col. 28, line 2, "glycerophosphorylcbolines," should read --glycerophosphorylcholines--.

Col. 28, line 8: "sn-1-,2-acyl-3-" should read --sn-1,2-acyl-3- --.

Col. 28, line 12: "phosphoethamolarnine," should read --phosphoethanolamine,--.

Col. 28, line 13: "ethanolarnine," should read --ethanolamine,--.

Col. 28, line 13: "palmltoyl-" should read-- -palmitoyl- --.

Col. 28, line 15: "-palmltoyl-" should read-- -palmitoyl- --.

Col. 28, line 28: "monostearatc, "should read --monostearate,--.

Col. 28, line 28: "sorbitan-sesquisterate," should read --sorbitan-sesquistearate--.

Col. 28, line 30, "glyceryl-monoleate," should read --glyceryl-monooleate,--.

Col. 28, line 32, "decaglyceryl-monlinolate," should read --decaglyceryl-monolinolenate--.

Col. 28, line 46: "of, insulin" should read --of insulin--.

Col. 28, line 60: "polyoxyethylene-cholesterol" should read --polyoxyethanyl-cholesterol--.

Col. 29, line 10: "4-5-cholesten-3-" should read --4,5-cholesten-3- --.

Col. 29, line 31: "glycerophosphorylserine," should read --glycerophosphorylserines,--.

UNITED STATES PATENT AND TRADEMARK OFFICE
CERTIFICATE OF CORRECTION

PATENT NO. : 5,858,398
DATED : January 12, 1999
INVENTOR(S) : Young W. Cho

It is certified that error appears in the above-indentified patent and that said Letters Patent is hereby corrected as shown below:

Col. 29, line 37: "sn-1-,2-acyl-3-" should read --sn-1,2-acyl-3- --.

Col. 30, line 6: "-palmiltoyl-" should read -- -palmitoyl- --.

Col. 30, line 15: "sorbitan-monocapiylate," should read --sorbitan-monocaprylate, --.

Col. 30, line 17: "sesquisterate," should read --sesquistearate, --.

Col. 30, line 20: "glyceryl-monoleate," should read --glyceryl-monooleate,--.

Col. 30, line 22: "decaglyceryl-monolinolate," should read --decaglyceryl-monolinolenate, --.

Col. 30, line 25: "polyoxyethylene-cholesterol" should read --polyoxyethanyl-cholesterol--; and "cholesteryl" should read --cholesterol,--.

Signed and Sealed this

Sixth Day of March, 2001

Attest:

NICHOLAS P. GODICI

Attesting Officer

Acting Director of the United States Patent and Trademark Office